(12) United States Patent
Rehman et al.

(10) Patent No.: US 10,585,048 B2
(45) Date of Patent: Mar. 10, 2020

(54) METHOD OF DETERMINING A VALUE OF A PARAMETER OF INTEREST OF A TARGET FORMED BY A PATTERNING PROCESS

(71) Applicant: ASML NETHERLANDS B.V., Veldhoven (NL)

(72) Inventors: Samee Ur Rehman, Eindhoven (NL); Anagnostis Tsiatmas, Eindhoven (NL); Sergey Tarabrin, Eindhoven (NL); Joannes Jitse Venselaar, 's-Hertogenbosch (NL); Alexandru Onose, Eindhoven (NL); Mariya Vyacheslavivna Medvedyeva, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 16/385,651

(22) Filed: Apr. 16, 2019

(65) Prior Publication Data

US 2019/0323972 A1    Oct. 24, 2019

(30) Foreign Application Priority Data

Apr. 18, 2018 (EP) .................................... 18168041

(51) Int. Cl.
*G03F 7/20* (2006.01)
*G01N 21/95* (2006.01)
(Continued)

(52) U.S. Cl.
CPC ....... *G01N 21/9501* (2013.01); *G01N 21/956* (2013.01); *G03F 7/70625* (2013.01); *G03F 7/70633* (2013.01); *G03F 9/7003* (2013.01)

(58) Field of Classification Search
CPC .. G01B 11/27; G01B 11/272; G01N 21/9501; G01N 21/956; G03B 27/42;
(Continued)

(56) References Cited

U.S. PATENT DOCUMENTS

2006/0033921 A1    2/2006  Den Boef et al.
2006/0066855 A1    3/2006  Den Boef et al.
(Continued)

FOREIGN PATENT DOCUMENTS

WO    2009078708    6/2009
WO    2009106279    9/2009

OTHER PUBLICATIONS

International Search Report and Written Opinion issued in corresponding PCT Patent Application No. PCT/EP2019/059049, dated Jul. 15, 2019.
(Continued)

*Primary Examiner* — Colin W Kreutzer
(74) *Attorney, Agent, or Firm* — Pillsbury Winthrop Shaw Pittman LLP

(57) ABSTRACT

Methods of determining a value of a parameter of interest are disclosed. In one arrangement, a symmetric component and an asymmetric component of a detected pupil representation from illuminating a target are derived. A first metric characterizing the symmetric component and a second metric characterizing the asymmetric component vary non-monotonically as a function of the parameter of interest over a reference range of values of the parameter of interest. A combination of the derived symmetric component and the derived asymmetric component are used to identify a correct value from a plurality of candidate values of the parameter of interest.

21 Claims, 14 Drawing Sheets

(51) Int. Cl.
*G01N 21/956* (2006.01)
*G03F 9/00* (2006.01)

(58) Field of Classification Search
CPC .............. G03F 7/70616; G03F 7/70625; G03F 7/70633; G03F 7/70675; G03F 7/70683; G03F 9/7003; G03F 9/7046; G03F 9/7049; G03F 9/7076; G03F 9/7088
USPC .............. 355/67, 68, 77; 356/237.5, 399–401
See application file for complete search history.

(56) References Cited

U.S. PATENT DOCUMENTS

| | | |
|---|---|---|
| 2010/0201963 A1 | 8/2010 | Cramer et al. |
| 2011/0027704 A1 | 2/2011 | Cramer et al. |
| 2011/0043791 A1 | 2/2011 | Smilde et al. |
| 2011/0073775 A1 | 3/2011 | Setija et al. |
| 2012/0242970 A1 | 9/2012 | Smilde et al. |
| 2017/0059999 A1 | 3/2017 | Van Der Schaar et al. |
| 2017/0255738 A1 | 9/2017 | Van Leest et al. |

OTHER PUBLICATIONS

European Extended Search Report issued in corresponding European Patent Application No. 18168041.4, dated Oct. 31, 2018.

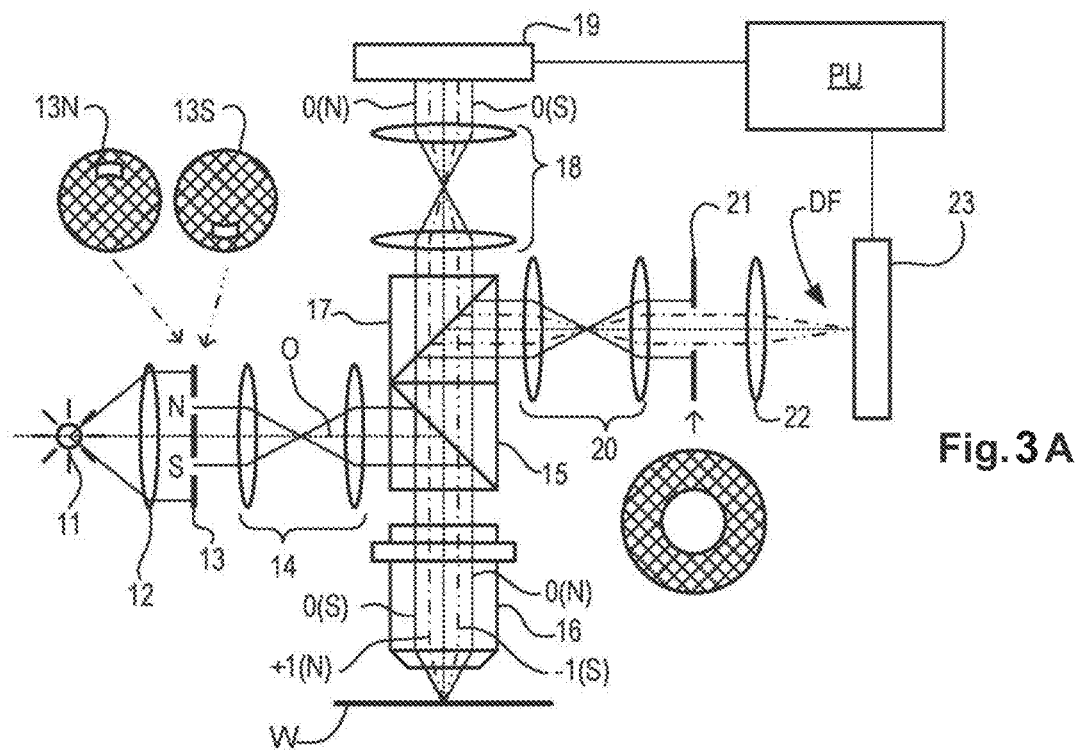
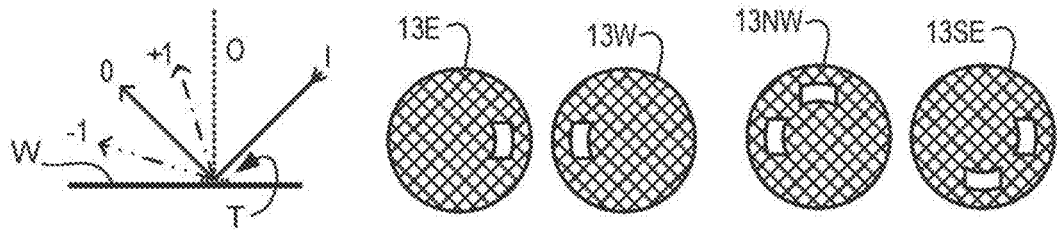
Fig. 3B  Fig. 3C  Fig. 3D
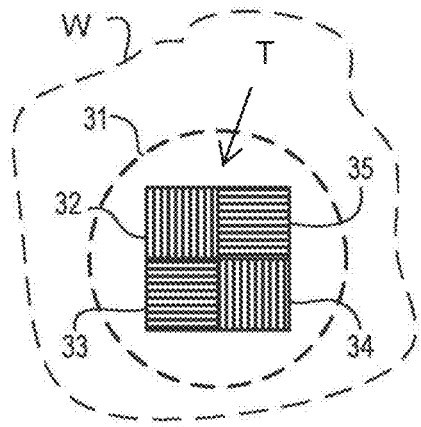
Fig. 4
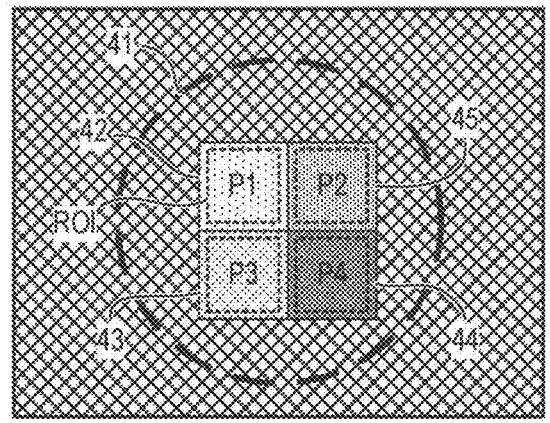
Fig. 5

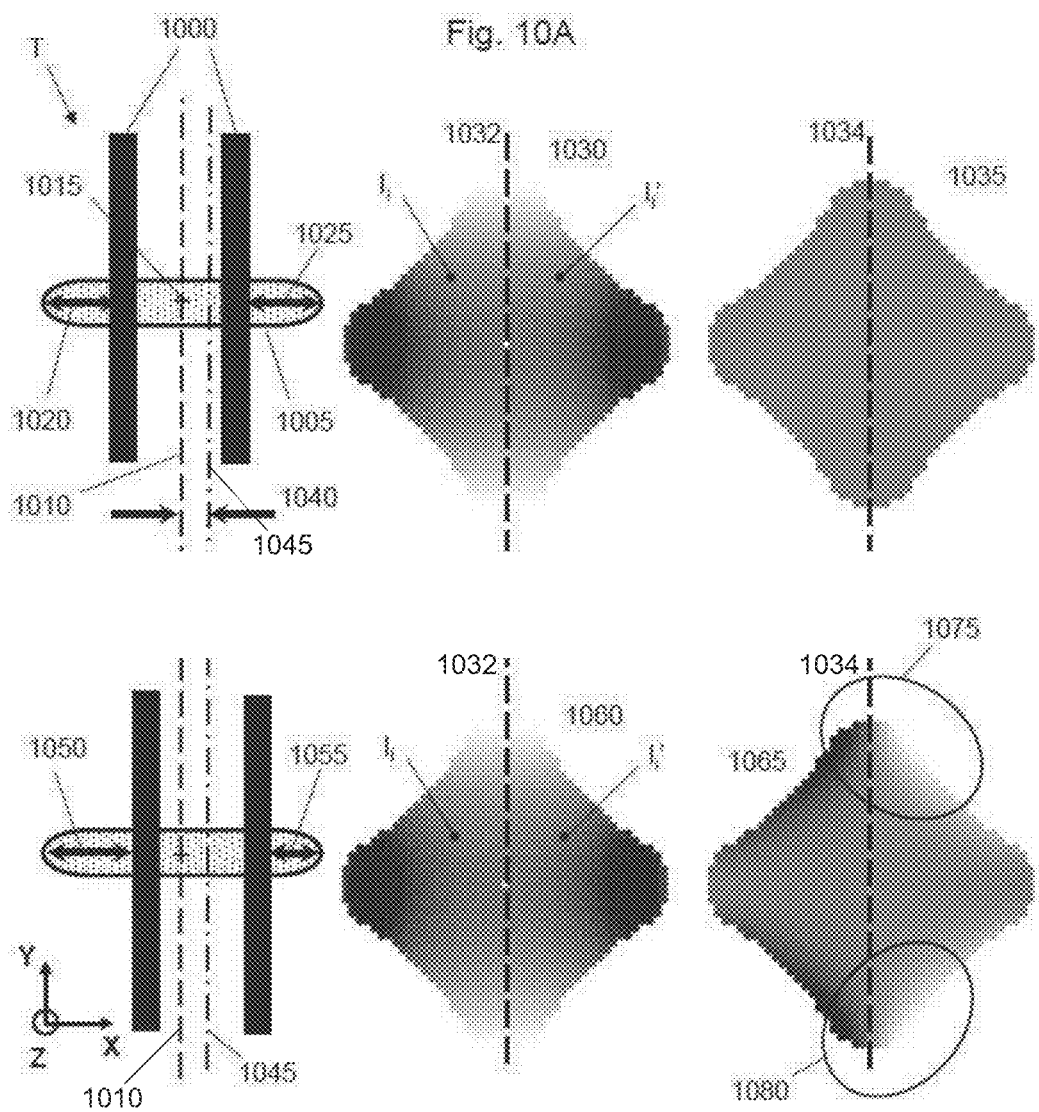

METHOD OF DETERMINING A VALUE OF A PARAMETER OF INTEREST OF A TARGET FORMED BY A PATTERNING PROCESS

This application claims the benefit of priority of European patent application no. 18168041.4, filed on Apr. 18, 2018. The foregoing application is incorporated herein in its entirety by reference.

FIELD

The present disclosure relates to determining a value of a parameter of interest of a target formed by a patterning process, such as a patterning process using lithography.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

Manufacturing devices, such as semiconductor devices, typically involves processing a substrate (e.g., a semiconductor wafer) using a number of fabrication processes to form various features and often multiple layers of the devices. Such layers and/or features are typically manufactured and processed using, e.g., deposition, lithography, etch, chemical-mechanical polishing, and ion implantation. Multiple devices may be fabricated on a plurality of dies on a substrate and then separated into individual devices. This device manufacturing process may be considered a patterning process. A patterning process involves a pattern transfer step, such as optical and/or nanoimprint lithography using a lithographic apparatus, to provide a pattern on a substrate and typically, but optionally, involves one or more related pattern processing steps, such as resist development by a development apparatus, baking of the substrate using a bake tool, etching the pattern by an etch apparatus, etc. Further, one or more metrology processes are involved in the patterning process.

Metrology processes are used at various steps during a patterning process to monitor and/or control the process. For example, metrology processes are used to measure one or more characteristics of a substrate, such as a relative location (e.g., registration, overlay, alignment, etc.) or dimension (e.g., line width, critical dimension (CD), thickness, etc.) of features formed on the substrate during the patterning process, such that, for example, the performance of the patterning process can be determined from the one or more characteristics. If the one or more characteristics are unacceptable (e.g., out of a predetermined range for the characteristic(s)), one or more variables of the patterning process may be designed or altered, e.g., based on the measurements of the one or more characteristics, such that substrates manufactured by the patterning process have an acceptable characteristic(s).

With the advancement of lithography and other patterning process technologies, the dimensions of functional elements have continually been reduced while the amount of the functional elements, such as transistors, per device has been steadily increased over decades. In the meanwhile, the requirement of accuracy in terms of overlay, critical dimension (CD), etc. has become more and more stringent. Error, such as error in overlay, error in CD, etc., will inevitably be produced in the patterning process. For example, imaging error may be produced from optical aberration, patterning device heating, patterning device error, and/or substrate heating and can be characterized in terms of, e.g., overlay, CD, etc. Additionally or alternatively, error may be introduced in other parts of the patterning process, such as in etch, development, bake, etc. and similarly can be characterized in terms of, e.g., overlay, CD, etc. The error may cause a problem in terms of the functioning of the device, including failure of the device to function or one or more electrical problems of the functioning device. Accordingly, it is desirable to be able to characterize one or more of these errors and take steps to design, modify, control, etc. a patterning process to reduce or minimize one or more of these errors Various tools are available for performing metrology processes, including various forms of scatterometer. These devices direct a beam of radiation onto a metrology target and measure one or more properties of the scattered radiation—e.g., intensity at a single angle of reflection, or over a range of angles of reflection, as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the metrology target by iterative approaches implemented using rigorous coupled wave analysis or finite element methods; library searches; and principal component analysis.

As the dimensions of functional elements become smaller, it is becoming increasingly challenging to measure values of parameters of interest sufficiently accurately and unambiguously.

SUMMARY

It is desirable to improve existing methods for measuring targets.

According to an aspect, there is provided a method of determining a value of a parameter of interest of a target formed by a patterning process on a substrate, the method comprising: deriving a symmetric component and an asymmetric component of a detected pupil representation, the detected pupil representation obtainable by performing a measurement process comprising illuminating the target with radiation and detecting radiation redirected by the target, wherein the target type and measurement process are such that a first metric characterizing the symmetric component and a second metric characterizing the asymmetric component vary non-monotonically as a function of the parameter of interest over a reference range of values of the parameter of interest; and using a combination of the derived symmetric component and the derived asymmetric component to identify: a correct value from a plurality of candidate values of the parameter of interest that all correspond, due to the non-monotonic variation of the first metric, to a value of the first metric corresponding to the derived symmetric component for the target; or a correct value from a plurality of candidate values of the parameter of interest that all correspond, due to the non-monotonic variation of the second metric, to a value of the second metric corresponding to the derived asymmetric component for the target.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 3A is a schematic diagram of a measurement apparatus for use in measuring targets according to an embodiment using a first pair of illumination apertures providing certain illumination modes;

FIG. 3B is a schematic detail of a diffraction spectrum of a target for a given direction of illumination;

FIG. 3C is a schematic illustration of a second pair of illumination apertures providing further illumination modes in using a measurement apparatus for diffraction-based overlay measurements;

FIG. 3D is a schematic illustration of a third pair of illumination apertures combining the first and second pairs of apertures providing further illumination modes in using a measurement apparatus for diffraction-based overlay measurements;

FIG. 4 schematically depicts a form of multiple periodic structure (e.g., multiple grating) target and an outline of a measurement spot on a substrate;

FIG. 5 schematically depicts an image of the target of FIG. 4 obtained in the apparatus of FIG. 3;

FIG. 10A schematically depicts an example unit cell, an associated pupil representation, and an associated derived pupil representation;

FIG. 10B schematically depicts an example unit cell, an associated pupil representation, and an associated derived pupil representation;

DETAILED DESCRIPTION OF EXEMPLARY EMBODIMENTS

Before describing embodiments in detail, it is instructive to present an example environment in which embodiments may be implemented.

Figure 1:
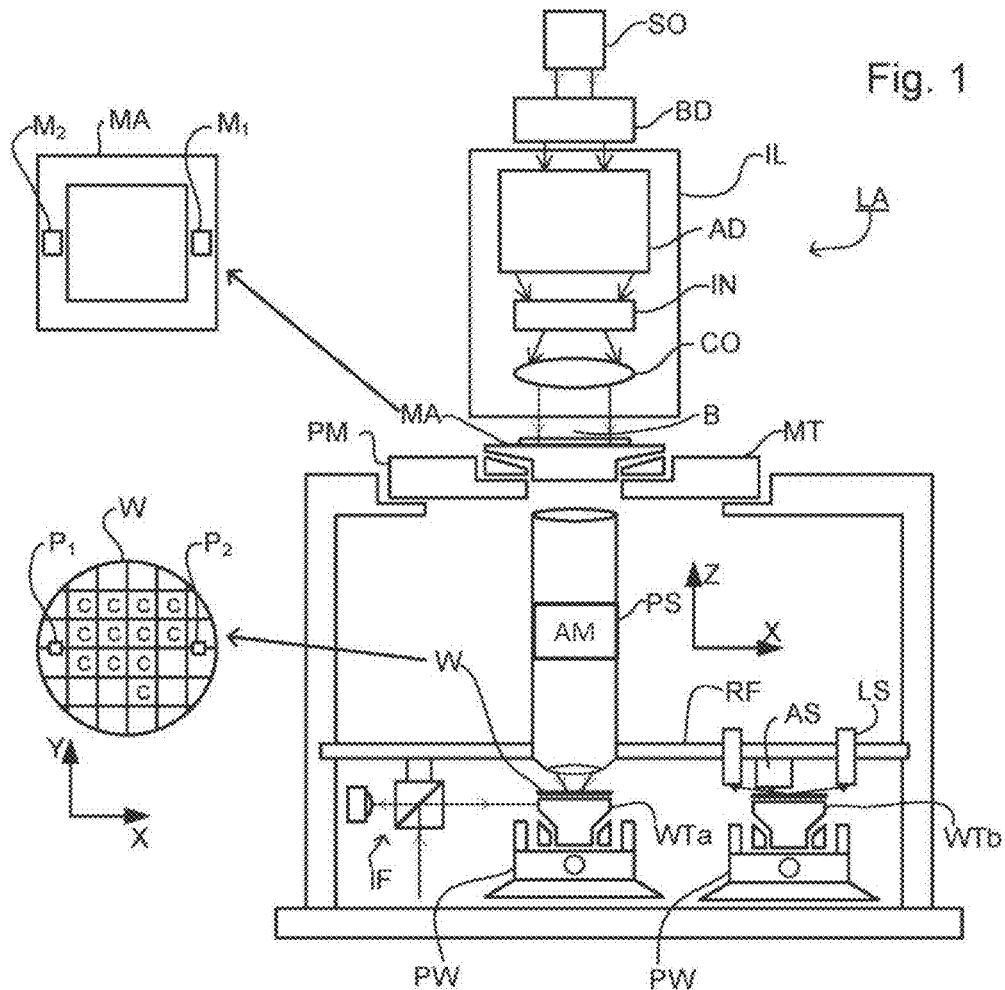
FIG. 1 schematically depicts an embodiment of a lithographic apparatus.

FIG. 1 schematically depicts a lithographic apparatus LA. The apparatus comprises:

an illumination system (illuminator) IL configured to condition a radiation beam B (e.g. UV radiation or DUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a pattern in a target portion of the substrate. In an embodiment, a patterning device is any device that can be used to impart a radiation beam with a pattern in its cross-section so as to create a pattern in a target portion of the substrate. It should be noted that the pattern imparted to the radiation beam may not exactly correspond to the desired pattern in the target portion of the substrate, for example if the pattern includes phase-shifting features or so-called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable Liquid Crystal Display (LCD) panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The projection system PS has an optical transfer function which may be non-uniform, which can affect the pattern imaged on the substrate W. For unpolarized radiation such effects can be fairly well described by two scalar maps, which describe the transmission (apodization) and relative phase (aberration) of radiation exiting the projection system PS as a function of position in a pupil plane thereof. These scalar maps, which may be referred to as the transmission map and the relative phase map, may be expressed as a linear combination of a complete set of basis functions. A particularly convenient set is the Zernike polynomials, which form a set of orthogonal polynomials defined on a unit circle. A determination of each scalar map may involve determining the coefficients in such an expansion. Since the Zernike polynomials are orthogonal on the unit circle, the Zernike coefficients may be determined by calculating the inner product of a measured scalar map with each Zernike polynomial in turn and dividing this by the square of the norm of that Zernike polynomial.

The transmission map and the relative phase map are field and system dependent. That is, in general, each projection system PS will have a different Zernike expansion for each field point (i.e. for each spatial location in its image plane). The relative phase of the projection system PS in its pupil plane may be determined by projecting radiation, for example from a point-like source in an object plane of the projection system PS (i.e. the plane of the patterning device MA), through the projection system PS and using a shearing interferometer to measure a wavefront (i.e. a locus of points with the same phase). A shearing interferometer is a common path interferometer and therefore, advantageously, no secondary reference beam is required to measure the wavefront. The shearing interferometer may comprise a diffraction grating, for example a two-dimensional grid, in an image plane of the projection system (i.e. the substrate table WT) and a detector arranged to detect an interference pattern in a plane that is conjugate to a pupil plane of the projection system PS. The interference pattern is related to the derivative of the phase of the radiation with respect to a coordinate in the pupil plane in the shearing direction. The detector may comprise an array of sensing elements such as, for example, charge coupled devices (CCDs).

The projection system PS of a lithography apparatus may not produce visible fringes and therefore the accuracy of the determination of the wavefront can be enhanced using phase stepping techniques such as, for example, moving the diffraction grating. Stepping may be performed in the plane of the diffraction grating and in a direction perpendicular to the scanning direction of the measurement. The stepping range may be one grating period, and at least three (uniformly distributed) phase steps may be used. Thus, for example, three scanning measurements may be performed in the y-direction, each scanning measurement being performed for a different position in the x-direction. This stepping of the diffraction grating effectively transforms phase variations into intensity variations, allowing phase information to be determined. The grating may be stepped in a direction perpendicular to the diffraction grating (z direction) to calibrate the detector.

The transmission (apodization) of the projection system PS in its pupil plane may be determined by projecting radiation, for example from a point-like source in an object plane of the projection system PS (i.e. the plane of the patterning device MA), through the projection system PS and measuring the intensity of radiation in a plane that is conjugate to a pupil plane of the projection system PS, using a detector. The same detector as is used to measure the wavefront to determine aberrations may be used.

The projection system PS may comprise a plurality of optical (e.g., lens) elements and may further comprise an adjustment mechanism AM configured to adjust one or more of the optical elements so as to correct for aberrations (phase variations across the pupil plane throughout the field). To achieve this, the adjustment mechanism may be operable to manipulate one or more optical (e.g., lens) elements within the projection system PS in one or more different ways. The projection system may have a coordinate system wherein its optical axis extends in the z direction. The adjustment mechanism may be operable to do any combination of the following: displace one or more optical elements; tilt one or more optical elements; and/or deform one or more optical elements. Displacement of an optical element may be in any direction (x, y, z or a combination thereof). Tilting of an optical element is typically out of a plane perpendicular to the optical axis, by rotating about an axis in the x and/or y directions although a rotation about the z axis may be used for a non-rotationally symmetric aspherical optical element. Deformation of an optical element may include a low frequency shape (e.g. astigmatic) and/or a high frequency shape (e.g. free form aspheres). Deformation of an optical element may be performed for example by using one or more actuators to exert force on one or more sides of the optical element and/or by using one or more heating elements to heat one or more selected regions of the optical element. In general, it may not be possible to adjust the projection system PS to correct for apodization (transmission variation across the pupil plane). The transmission map of a projection system PS may be used when designing a patterning device (e.g., mask) MA for the lithography apparatus LA. Using a computational lithography technique, the patterning device MA may be designed to at least partially correct for apodization.

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
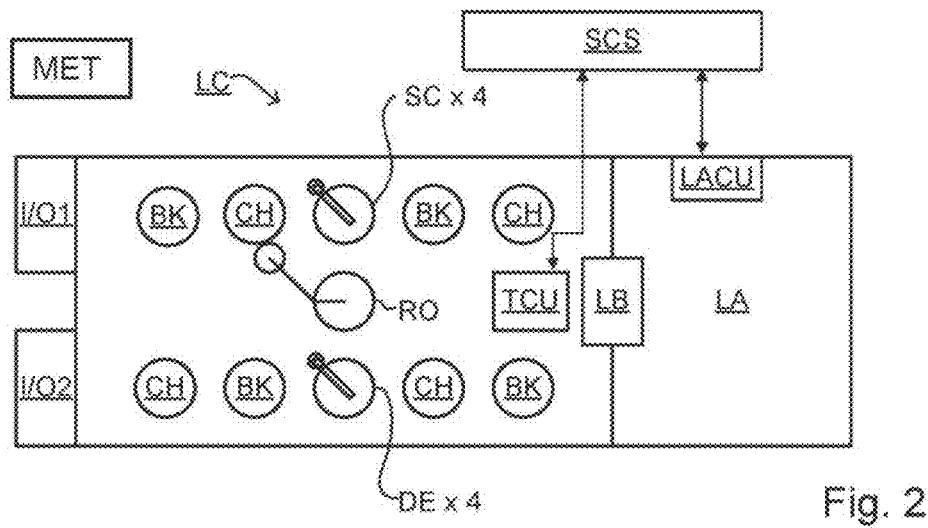
FIG. 2 schematically depicts an embodiment of a lithographic cell or cluster.

As shown in FIG. 2, the lithographic apparatus LA may form part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1, I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU.

Thus, the different apparatuses can be operated to maximize throughput and processing efficiency.

In order that a substrate that is exposed by the lithographic apparatus is exposed correctly and consistently, it is desirable to inspect an exposed substrate to measure or determine one or more properties such as overlay (which can be, for example, between structures in overlying layers or between structures in a same layer that have been provided separately to the layer by, for example, a double patterning process), line thickness, critical dimension (CD), focus offset, a material property, etc. Accordingly a manufacturing facility in which lithocell LC is located also typically includes a metrology system MET which receives some or all of the substrates W that have been processed in the lithocell. The metrology system MET may be part of the lithocell LC, for example it may be part of the lithographic apparatus LA.

Metrology results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology system MET, a metrology apparatus is used to determine one or more properties of the substrate, and in particular, how one or more properties of different substrates vary or different layers of the same substrate vary from layer to layer. The metrology apparatus may be integrated into the lithographic apparatus LA or the lithocell LC or may be a stand-alone device. To enable rapid measurement, it is desirable that the metrology apparatus measure one or more properties in the exposed resist layer immediately after the exposure. However, the latent image in the resist has a low contrast—there is only a very small difference in refractive index between the parts of the resist which have been exposed to radiation and those which have not—and not all metrology apparatuses have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

To enable the metrology, one or more targets can be provided on the substrate. In an embodiment, the target is specially designed and may comprise a periodic structure. In an embodiment, the target is a part of a device pattern, e.g., a periodic structure of the device pattern. In an embodiment, the device pattern is a periodic structure of a memory device (e.g., a Bipolar Transistor (BPT), a Bit Line Contact (BLC), etc. structure).

In an embodiment, the target on a substrate may comprise one or more 1-D periodic structures (e.g., gratings), which are printed such that after development, the periodic structural features are formed of solid resist lines. In an embodiment, the target may comprise one or more 2-D periodic structures (e.g., gratings), which are printed such that after development, the one or more periodic structures are formed of solid resist pillars or vias in the resist. The bars, pillars or vias may alternatively be etched into the substrate (e.g., into one or more layers on the substrate).

In an embodiment, one of the parameters of interest of a patterning process is overlay. Overlay can be measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay using dark-field detection of the diffraction orders enables overlay measurements on smaller targets. These targets can be smaller than the illumination spot and may be surrounded by device product structures on a substrate. In an embodiment, multiple targets can be measured in one radiation capture.

A metrology apparatus suitable for use in embodiments to measure, e.g., overlay is schematically shown in FIG. 3A. A target T (comprising a periodic structure such as a grating) and diffracted rays are illustrated in more detail in FIG. 3B. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective lens 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis illumination from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode may interfere with the desired measurement signals.

As shown in FIG. 3B, target T is placed with substrate W substantially normal to the optical axis O of objective lens 16. A ray of illumination I impinging on target T from an angle off the axis O gives rise to a zeroth order ray (solid line 0) and two first order rays (dot-chain line +1 and double dot-chain line −1). With an overfilled small target T, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective lens are closely aligned with the central optical axis. The rays illustrated in FIGS. 3A and 3B are shown somewhat off axis, purely to enable them to be more easily distinguished in the diagram. At least the 0 and +1 orders diffracted by the target on substrate W are collected by objective lens 16 and directed back through prism 15.

Returning to FIG. 3A, both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16. Thus, in an embodiment, measurement results are obtained by measuring the target twice under certain conditions, e.g., after rotating the target or changing the illumination mode or changing the imaging mode to obtain separately the −1st and the +1st diffraction order intensities. Comparing these intensities for a given target provides a measurement of asymmetry in the target, and asymmetry in the target can be used as an indicator of a parameter of a lithography process, e.g., overlay. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements. The pupil plane image can also be used for other measurement purposes such as reconstruction, as described further hereafter.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane of the objective lens 16. Aperture stop 21 functions to block the zeroth order diffracted beam so that the image of the target formed on sensor 23 is formed from the −1 or +1 first order beam. Data regarding the images measured by sensors 19 and 23 are output to processor and controller PU, the function of which will depend on the particular type of measurements being performed. Note that the term 'image' is used in a broad sense. An image of the periodic structure features (e.g., grating lines) as such will not be formed, if only one of the −1 and +1 orders is present.

The particular forms of aperture plate 13 and stop 21 shown in FIG. 3 are purely examples. In another embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Note that aperture plate 13N or 13S are used to measure a periodic structure of a target oriented in one direction (X or Y depending on the set-up). For measurement of an orthogonal periodic structure, rotation of the target through 90° and 270° might be implemented. Different aperture plates are shown in FIGS. 3C and D. FIG. 3C illustrates two further types of off-axis illumination mode. In a first illumination mode of FIG. 3C, aperture plate 13E provides off-axis illumination from a direction designated, for the sake of description only, as 'east' relative to the 'north' previously described. In a second illumination mode of FIG. 3C, aperture plate 13W is used to provide similar illumination, but from an opposite direction, labeled 'west'. FIG. 3D illustrates two further types of off-axis illumination mode. In a first illumination mode of FIG. 3D, aperture plate 13NW provides off-axis illumination from the directions designated 'north' and 'west' as previously described. In a second illumination mode, aperture plate 13SE is used to provide similar illumination, but from an opposite direction, labeled 'south' and 'east' as previously described. The use of these, and numerous other variations and applications of the apparatus are described in, for example, the prior published patent application publications mentioned above.

FIG. 4 depicts an example composite metrology target T formed on a substrate. The composite target comprises four periodic structures (in this case, gratings) 32, 33, 34, 35 positioned closely together. In an embodiment, the periodic structure layout may be made smaller than the measurement spot (i.e., the periodic structure layout is overfilled). Thus, in an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures (e.g., composite gratings) formed by overlying periodic structures, i.e., periodic structures are patterned in different layers of the device formed on substrate W and such that at least one periodic structure in one layer overlays at least one periodic structure in a different layer. Such a target may have outer dimensions within 20 μm×20 μm or within 16 μm×16 μm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the different bias facilitates distinguishing between the layer pairs.

Returning to FIG. 4, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in an image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3D. While the sensor 19 cannot resolve the different individual periodic structures 32 to 35, the sensor 23 can do so. The dark rectangle represents the field of the image on the sensor, within which the illuminated spot 31 on the substrate is imaged into a corresponding circular area 41. Within this, rectangular areas 42-45 represent the images of the periodic structures 32 to 35. The target can be positioned in among device product features, rather than or in addition to in a scribe lane. If the periodic structures are located in device product areas, device features may also be visible in the periphery of this image field. Processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an example of such a parameter.

Figure 6:
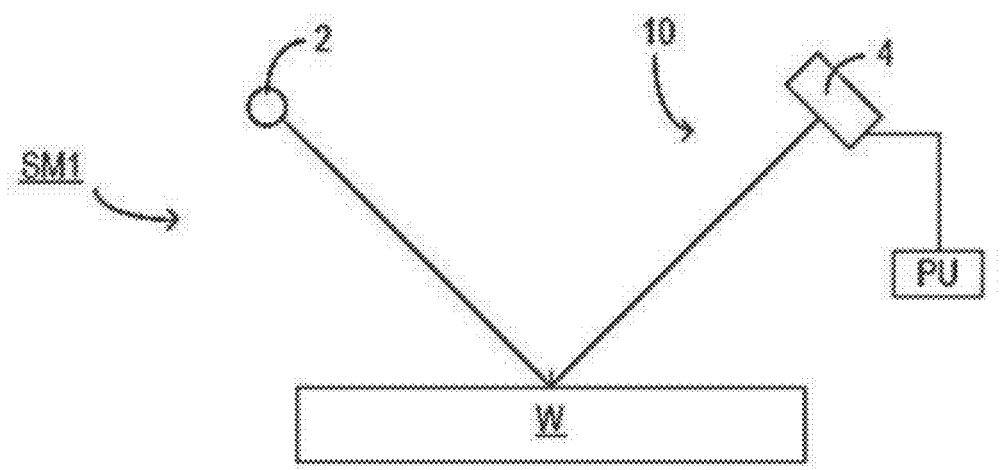
FIG. 6 schematically depicts an example of a metrology apparatus and metrology technique.
Figure 6:
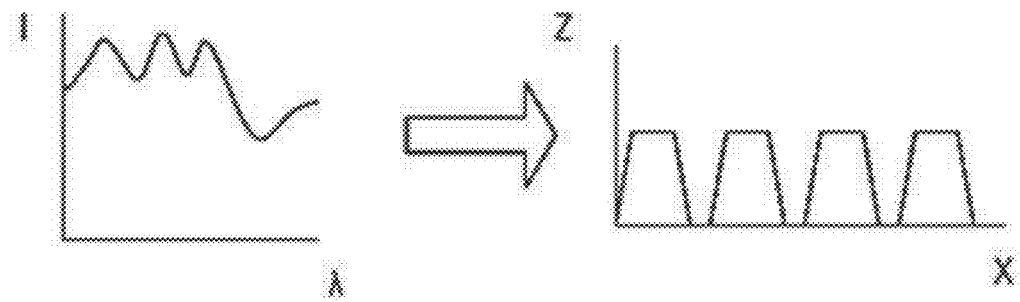

In an embodiment, one of the parameters of interest of a patterning process is feature width (e.g., CD). FIG. 6 depicts a highly schematic example metrology apparatus (e.g., a scatterometer) that can enable feature width determination. It comprises a broadband (white light) radiation projector 2 which projects radiation onto a substrate W. The redirected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 6. In general, for the reconstruction the general form of the structure is known and some variables are assumed from knowledge of the process by which the structure was made, leaving only a few variables of the structure to be determined from the measured data. Such a metrology apparatus may be configured as a normal-incidence metrology apparatus or an oblique-incidence metrology apparatus. Moreover, in addition to measurement of a parameter by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement in this manner are described, for example, in U.S. patent application publication US2006-066855, which is incorporated herein in its entirety.

Figure 7:
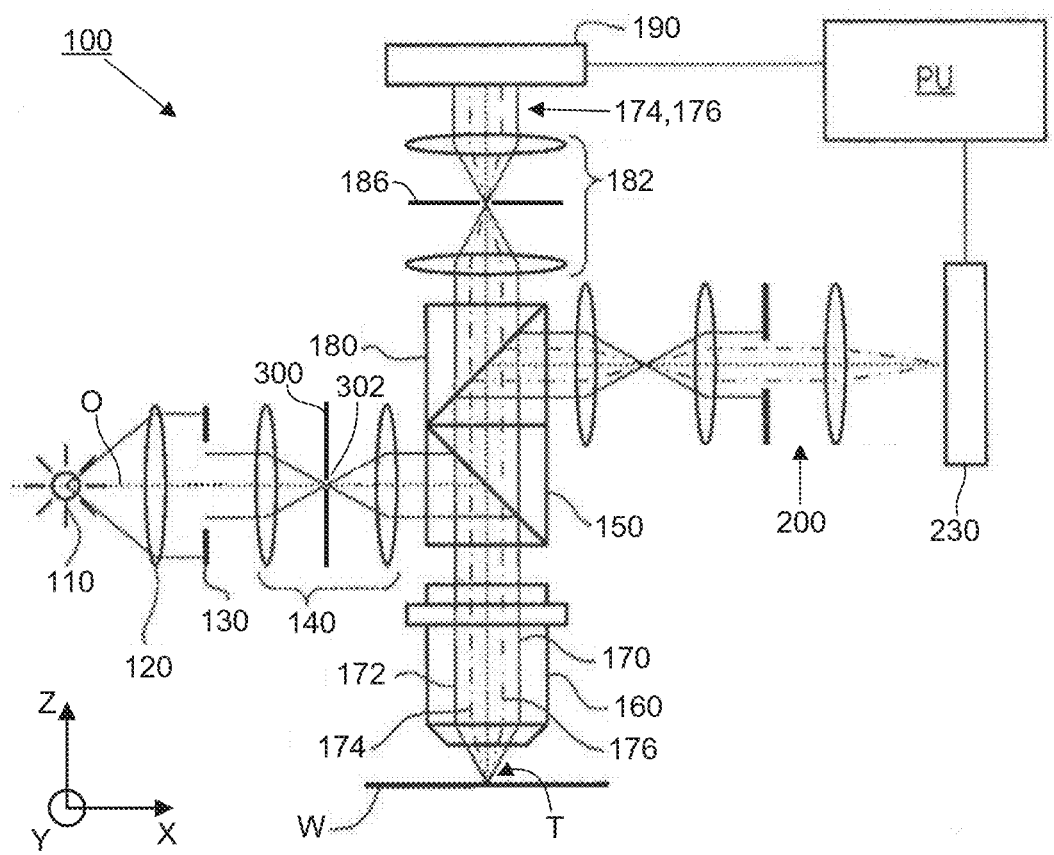
FIG. 7 schematically depicts an example of a metrology apparatus.

FIG. 7 illustrates an example of a metrology apparatus 100 suitable for use in embodiments of the present disclosure. The principles of operation of this type of metrology apparatus are explained in more detail in the U.S. Patent Application Nos. US 2006-033921 and US 2010-201963, which are incorporated herein in their entireties by reference. An optical axis, which has several branches throughout the apparatus, is represented by a dotted line O. In this apparatus, radiation emitted by source 110 (e.g., a xenon lamp) is directed onto substrate W via by an optical system comprising: lens system 120, aperture plate 130, lens system 140, a partially reflecting surface 150 and objective lens 160. In an embodiment these lens systems 120, 140, 160 are arranged in a double sequence of a 4F arrangement. In an embodiment, the radiation emitted by radiation source 110 is collimated using lens system 120. A different lens arrangement can be used, if desired. The angular range at which the radiation is incident on the substrate can be selected by defining a spatial intensity distribution in a plane that presents the spatial spectrum of the substrate plane. In particular, this can be done by inserting an aperture plate 130 of suitable form between lenses 120 and 140, in a plane which is a back-projected image of the objective lens pupil plane. Different intensity distributions (e.g., annular, dipole, etc.) are possible by using different apertures. The angular distribution of illumination in radial and peripheral directions, as well as properties such as wavelength, polarization and/or coherency of the radiation, can all be adjusted to obtain desired results. For example, one or more interference filters 130 (see FIG. 9) can be provided between source 110 and partially reflecting surface 150 to select a wavelength of interest in the range of, say, 400-900 nm or even lower, such as 200-300 nm. The interference filter may be tunable rather than comprising a set of different filters. A grating could be used instead of an interference filter. In an embodiment, one or more polarizers 170 (see FIG. 9) can be provided between source 110 and partially reflecting surface 150 to select a polarization of interest. The polarizer may be tunable rather than comprising a set of different polarizers.

As shown in FIG. 7, the target T is placed with substrate W normal to the optical axis O of objective lens 160. Thus, radiation from source 110 is reflected by partially reflecting surface 150 and focused into an illumination spot S (see FIG. 8) on target T on substrate W via objective lens 160. In an embodiment, objective lens 160 has a high numerical aperture (NA), desirably at least 0.9 or at least 0.95. An immersion metrology apparatus (using a relatively high refractive index fluid such as water) may even have a numerical aperture over 1.

Rays of illumination 170, 172 focused to the illumination spot from angles off the axis O gives rise to diffracted rays 174, 176. It should be remembered that these rays are just one of many parallel rays covering an area of the substrate including target T. Each element within the illumination spot is within the field of view of the metrology apparatus. Since the aperture in plate 130 has a finite width (necessary to admit a useful quantity of radiation), the incident rays 170, 172 will in fact occupy a range of angles, and the diffracted rays 174, 176 will be spread out somewhat. According to the point spread function of a small target, each diffraction order will be further spread over a range of angles, not a single ideal ray as shown.

At least the $0^{th}$ order diffracted by the target on substrate W is collected by objective lens 160 and directed back through partially reflecting surface 150. An optical element 180 provides at least part of the diffracted beams to optical system 182 which forms a diffraction spectrum (pupil plane image) of the target T on sensor 190 (e.g. a CCD or CMOS sensor) using the zeroth and/or first order diffractive beams. In an embodiment, an aperture 186 is provided to filter out certain diffraction orders so that a particular diffraction order is provided to the sensor 190. In an embodiment, the aperture 186 allows substantially or primarily only zeroth order radiation to reach the sensor 190. In an embodiment, the sensor 190 may be a two-dimensional detector so that a two-dimensional angular scatter spectrum of a substrate target T can be measured. The sensor 190 may be, for example, an array of CCD or CMOS sensors, and may use an integration time of, for example, 40 milliseconds per frame. The sensor 190 may be used to measure the intensity of redirected radiation at a single wavelength (or narrow wavelength range), the intensity separately at multiple wavelengths or integrated over a wavelength range. Furthermore, the sensor may be used to separately measure the intensity of radiation with transverse magnetic- and/or transverse electric-polarization and/or the phase difference between transverse magnetic- and transverse electric-polarized radiation.

Optionally, optical element 180 provides at least part of the diffracted beams to measurement branch 200 to form an image of the target on the substrate W on a sensor 230 (e.g. a CCD or CMOS sensor). The measurement branch 200 can be used for various auxiliary functions such as focusing the metrology apparatus (i.e., enabling the substrate W to be in focus with the objective 160), and/or for dark field imaging of the type mentioned in the introduction.

In order to provide a customized field of view for different sizes and shapes of grating, an adjustable field stop 300 is provided within the lens system 140 on the path from source 110 to the objective lens 160. The field stop 300 contains an aperture 302 and is located in a plane conjugate with the plane of the target T, so that the illumination spot becomes an image of the aperture 302. The image may be scaled according to a magnification factor, or the aperture and illumination spot may be in 1:1 size relation. In order to make the illumination adaptable to different types of measurement, the aperture plate 300 may comprise a number of aperture patterns formed around a disc, which rotates to bring a desired pattern into place. Alternatively or in addition, a set of plates 300 could be provided and swapped, to achieve the same effect. Additionally or alternatively, a programmable aperture device such as a deformable mirror array or transmissive spatial light modulator can be used also.

Typically, a target will be aligned with its periodic structure features running either parallel to the Y axis or parallel to the X axis. With regard to its diffractive behavior, a periodic structure with features extending in a direction parallel to the Y axis has periodicity in the X direction, while a periodic structure with features extending in a direction parallel to the X axis has periodicity in the Y direction. In order to measure the performance in both directions, both types of features are generally provided. While for simplicity there will be reference to lines and spaces, the periodic structure need not be formed of lines and space. Moreover, each line and/or space between lines may be a structure formed of smaller sub-structures. Further, the periodic structure may be formed with periodicity in two dimensions at once, for example where the periodic structure comprises posts and/or via holes.

Figure 8:
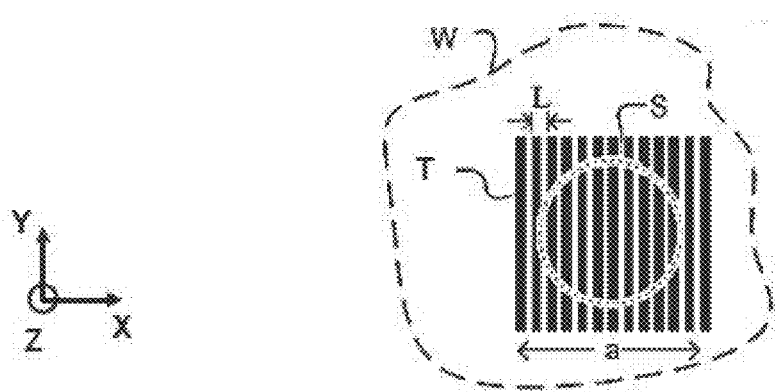
FIG. 8 illustrates the relationship between an illumination spot of a metrology apparatus and a metrology target.

FIG. 8 illustrates a plan view of a typical target T, and the extent of illumination spot S in the apparatus of FIG. 7. To obtain a diffraction spectrum that is free of interference from surrounding structures, the target T, in an embodiment, is a periodic structure (e.g., grating) larger than the width (e.g., diameter) of the illumination spot S. The width of spot S may be smaller than the width and length of the target. The target in other words is 'underfilled' by the illumination, and the diffraction signal is essentially free from any signals from product features and the like outside the target itself. This simplifies mathematical reconstruction of the target as it can be regarded as infinite. In other embodiments, as described below, the target may not be fully underfilled and/or misalignment of the radiation spot relative to the target may cause features outside of the target to contribute to the signal.

Figure 9:
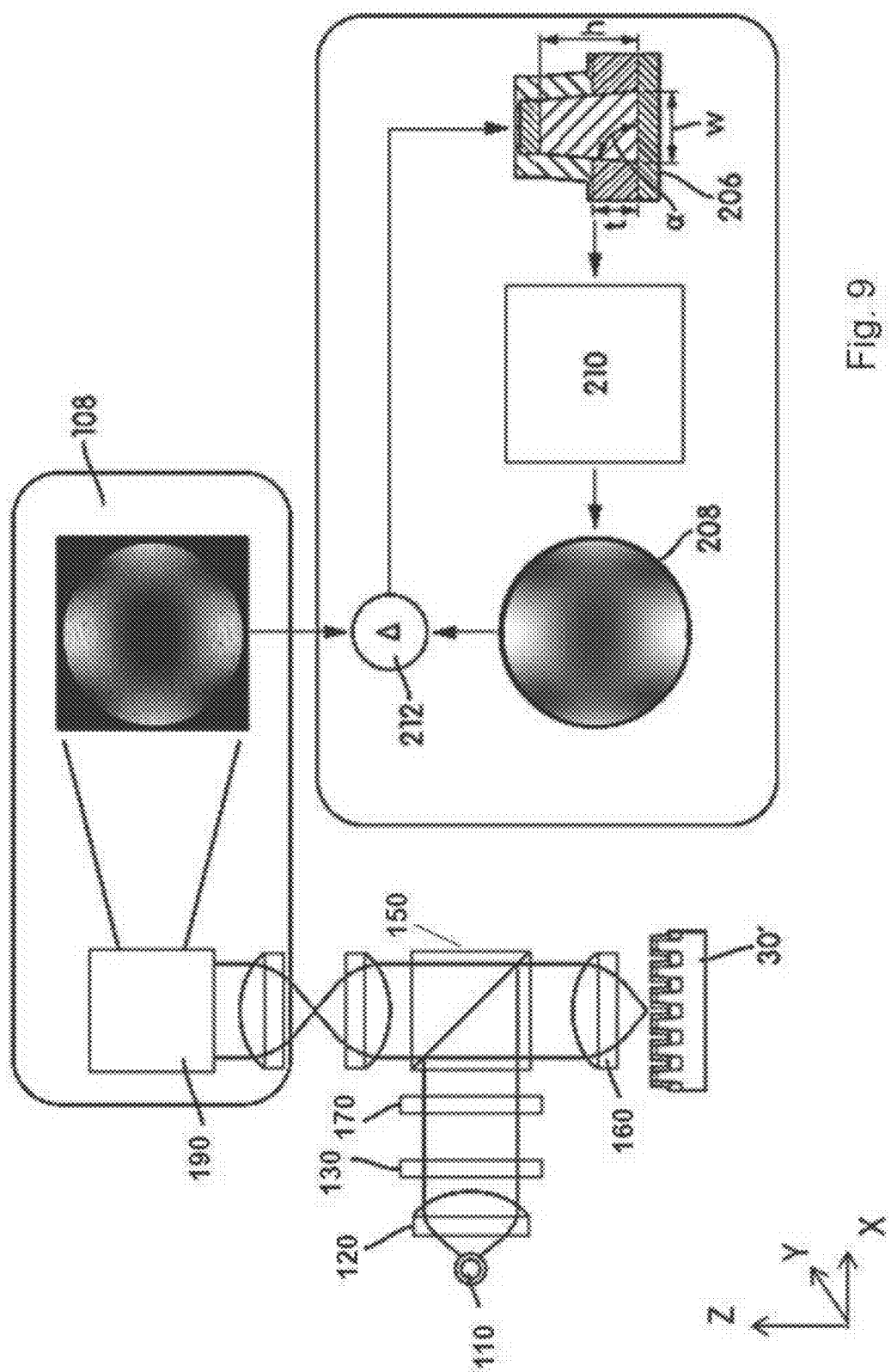
FIG. 9 schematically depicts a process of deriving one or more variables of interest based on measurement data.

FIG. 9 schematically depicts an example process of the determination of the value of one or more variables (also referred to as parameters) of interest of a target pattern 30' based on measurement data obtained using metrology. Radiation detected by the detector 190 provides a measured radiation distribution 108 for target 30'.

For the given target 30', a radiation distribution 208 can be computed/simulated from a parameterized mathematical model 206 using, for example, a numerical Maxwell solver 210. The parameterized mathematical model 206 shows example layers of various materials making up, and associated with, the target. The parameterized mathematical model 206 may include one or more of variables for the features and layers of the portion of the target under consideration, which may be varied and derived. As shown in FIG. 9, the one or more of the variables may include the thickness t of one or more layers, a width w (e.g., CD) of one or more features, a height h of one or more features, a sidewall angle a of one or more features, and/or relative position between features (herein considered overlay). Although not shown, the one or more of the variables may further include, but is not limited to, the refractive index (e.g., a real or complex refractive index, refractive index tensor, etc.) of one or more of the layers, the extinction coefficient of one or more layers, the absorption of one or more layers, resist loss during development, a footing of one or more features, and/or line edge roughness of one or more features. One or more values of one or more parameters of a 1-D periodic structure or a 2-D periodic structure, such as a value of width, length, shape or a 3-D profile characteristic, may be input to the reconstruction process from knowledge of the patterning process and/or other measurement processes. For example, the initial values of the variables may be those expected values of one or more parameters, such as a value of CD, pitch, etc., for the target being measured.

In some cases, a target can be divided into a plurality of instances of a unit cell. To help ease computation of the radiation distribution of a target in that case, the model 206 can be designed to compute/simulate using the unit cell of the structure of the target, where the unit cell is repeated as instances across the full target. Thus, the model 206 can compute using one unit cell and copy the results to fit a whole target using appropriate boundary conditions in order to determine the radiation distribution of the target.

Additionally or alternatively to computing the radiation distribution 208 at the time of reconstruction, a plurality of radiation distributions 208 can be pre-computed for a plurality of variations of variables of the target portion under consideration to create a library of radiation distributions for use at the time of reconstruction.

The measured radiation distribution 108 is then compared at 212 to the computed radiation distribution 208 (e.g., computed near that time or obtained from a library) to determine the difference between the two. If there is a difference, the values of one or more of the variables of the parameterized mathematical model 206 may be varied, a new computed radiation distribution 208 obtained (e.g., calculated or obtained from a library) and compared against the measured radiation distribution 108 until there is sufficient match between the measured radiation distribution 108 and the radiation distribution 208. At that point, the values of the variables of the parameterized mathematical model 206 provide a good or best match of the geometry of the actual target 30'. In an embodiment, there is sufficient match when a difference between the measured radiation distribution 108 and the computed radiation distribution 208 is within a tolerance threshold.

In these metrology apparatuses, a substrate support may be provided to hold the substrate W during measurement operations. The substrate support may be similar or identical in form to the substrate table WT of FIG. 1. In an example where the metrology apparatus is integrated with the lithographic apparatus, it may even be the same substrate table. Coarse and fine positioners may be provided to accurately position the substrate in relation to a measurement optical system. Various sensors and actuators are provided for example to acquire the position of a target of interest, and to bring it into position under the objective lens. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

In an embodiment, the measurement accuracy and/or sensitivity of a target may vary with respect to one or more attributes of the beam of radiation provided onto the target, for example, the wavelength of the radiation beam, the polarization of the radiation beam, the intensity distribution (i.e., angular or spatial intensity distribution) of the radiation beam, etc. Thus, a particular measurement strategy can be selected that desirably obtains, e.g., good measurement accuracy and/or sensitivity of the target.

In order to monitor the patterning process (e.g., a device manufacturing process) that includes at least one pattern transfer step (e.g., an optical lithography step), the patterned substrate is inspected and one or more parameters of the patterned substrate are measured/determined. The one or more parameters may include, for example, overlay between successive layers formed in or on the patterned substrate, critical dimension (CD) (e.g., critical linewidth) of, for example, features formed in or on the patterned substrate, focus or focus error of an optical lithography step, dose or dose error of an optical lithography step, optical aberrations of an optical lithography step, placement error (e.g., edge placement error), etc. This measurement may be performed on a target of the product substrate itself and/or on a dedicated metrology target provided on the substrate. The measurement can be performed after-development of a resist but before etching or can be performed after-etch.

There are various techniques for making measurements of the structures formed in the patterning process, including the use of a scanning electron microscope, an image-based measurement tool and/or various specialized tools. As discussed above, a fast and non-invasive form of specialized metrology tool is one in which a beam of radiation is directed onto a target on the surface of the substrate and properties of the scattered (diffracted/reflected) beam are measured. By evaluating one or more properties of the radiation scattered by the substrate, one or more properties of the substrate can be determined. This may be termed diffraction-based metrology. One such application of this diffraction-based metrology is in the measurement of feature asymmetry within a target. This can be used as a measure of overlay, for example, but other applications are also known. For example, asymmetry can be measured by comparing opposite parts of the diffraction spectrum (for example, comparing the $-1$st and $+1^{st}$ orders in the diffraction spectrum of a periodic grating). This can be done as described above and as described, for example, in U.S. patent application publication US2006-066855, which is incorporated herein in its entirety by reference. Another application of diffraction-based metrology is in the measurement of feature width (CD) within a target. Such techniques can use the apparatus and methods described above in respect of FIGS. 6-9.

Now, while these techniques are effective, it is desirable to provide an alternative measurement technique that derives feature asymmetry within a target (such as overlay, CD asymmetry, sidewall angle asymmetry, etc.). This technique can be effective for specially designed metrology targets or perhaps more significantly, for determining feature asymmetry directly on a device pattern.

Figure 10C:
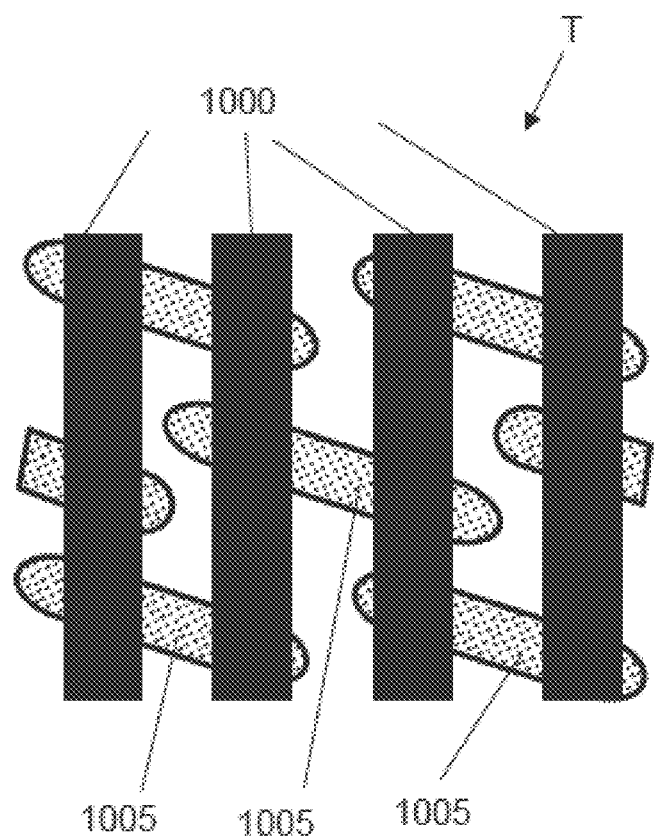
FIG. 10C schematically depicts an example target comprising one or more physical instances of a unit cell.

Referring to FIG. 10, principles of this measurement technique are described in the context of an overlay embodiment. In FIG. 10A, a geometrically symmetric unit cell of a target T is shown. The target T can comprise just a single physical instance of a unit cell or can comprise a plurality of physical instances of the unit cell as shown in FIG. 10C.

The target T can be a specially designed target. In an embodiment, the target is for a scribe lane. In an embodiment, the target can be an in-die target, i.e., the target is among the device pattern (and thus between the scribe lanes). In an embodiment, the target can have a feature width or pitch comparable to device pattern features. For example, the target feature width or pitches can be less than or equal to 300% of the smallest feature size or pitch of the device pattern, be less than or equal to 200% of the smallest feature size or pitch of the device pattern, be less than or equal to 150% of the smallest feature size or pitch of the device pattern, or be less than or equal to 100% of the smallest feature size or pitch of the device pattern.

The target T can be a device structure. For example, the target T can be a portion of a memory device (which often has one or more structures that are, or can be, geometrically symmetric as discussed further below).

In an embodiment, the target T or a physical instance of the unit cell can have an area of less than or equal to 2400 square microns, an area of less than or equal to 2000 square microns, an area of less than or equal to 1500 square microns, an area of less than or equal to 1000 square microns, an area of less than or equal to 400 square microns, less than or equal to 200 square microns, less than or equal to 100 square microns, less than or equal to 50 square microns, less than or equal to 25 square microns, less than or equal to 10 square microns, less than or equal to 5 square microns, less than or equal to 1 square micron, less than or equal to 0.5 square microns, or less than or equal to 0.1 square microns. In an embodiment, the target T or a physical instance of the unit cell has a cross-sectional dimension parallel to the plane of the substrate of less than or equal to 50 microns, less than or equal to 30 microns, less than or equal to 20 microns, less than or equal to 15 microns, less than or equal to 10 microns, less than or equal to 5 microns, less than or equal to 3 microns, less than or equal to 1 micron, less than or equal to 0.5 microns, less than or equal to 0.2 microns, or less than or equal to 0.1 microns.

In an embodiment, the target T or a physical instance of the unit cell has a pitch of structures of less than or equal to less than or equal to 5 microns, less than or equal to 2 microns, less than or equal to 1 micron, less than or equal to 500 nm, less than or equal to 400 nm, less than or equal to 300 nm, less than or equal to 200 nm, less than or equal to 150 nm, less than or equal to 100 nm, less than or equal to 75 nm, less than or equal to 50 nm, less than or equal to 32 nm, less than or equal to 22 nm, less than or equal to 16 nm, less than or equal to 10 nm, less than or equal to 7 nm or less than or equal to 5 nm.

In an embodiment, the target T has a plurality of physical instances of the unit cell. Thus, a target T could typically have the higher dimensions listed here, while the physical instances of the unit cell will have the lower dimensions listed here. In an embodiment, the target T comprises 50,000 or more physical instances of the unit cell, 25,000 or more physical instances of the unit cell, 15,000 or more physical instances of the unit cell, 10,000 or more physical instances of the unit cell, 5,000 or more physical instances of the unit cell, 1000 or more physical instances of the unit cell, 500 or more physical instances of the unit cell, 200 or more physical instances of the unit cell, 100 or more physical instances of the unit cell, 50 or more physical instances of the unit cell, or 10 or more physical instances of the unit cell.

Desirably, the physical instance of the unit cell or the plurality of physical instances of the unit cell collectively fills a beam spot of the metrology apparatus. In that case, the measured results comprise essentially only information from the physical instance of the unit cell (or its plurality of instances). In an embodiment, the beam spot has a cross-sectional width of 50 microns or less, 40 microns or less, 30 microns or less, 20 microns or less, 15 microns or less, 10 microns or less, 5 microns or less, or 2 microns or less.

The unit cell in FIG. 10A comprises at least two structures that are, or will be, physically instantiated on the substrate. A first structure 1000 comprises lines and a second structure 1005 comprises an oval-type shape. Of course, the first and second structures 1000, 1005 can be different structures than depicted.

Further, in this example, there can be a relative shift between the first and second structures 1000, 1005 from their expected position due to their separate transfer onto the substrate so as to have an error in overlay. In this example, the first structure 1000 is located in a higher layer on a substrate than the second structure 1005. Thus, in an embodiment, the second structure 1005 can be produced in a first lower layer in a first execution of a patterning process and the first structure 1000 can be produced in a second higher layer than the first lower layer in a second execution of the patterning process. Now, it is not necessary that the first and second structures 1000, 1005 be located in different layers. For example, in a double patterning process (including, for example, an etching process as part thereof), the first and second structures 1000, 1005 could be produced in a same layer to form essentially a single pattern but there could still be an "overlay" concern in terms of their relative placement within the same layer. In this single layer example, both the first and second structures 1000, 1005 could have, for example, the form of lines like shown in FIG. 10A for the first structure 1000 but the lines of the second structure 1005, already provided on the substrate by a first pattern transfer process, could be interleaved with the lines of the structure 1000 provided in a second pattern transfer process.

Significantly, the unit cell has, or is capable of having, a geometric symmetry with respect to an axis or point. For example, the unit cell in FIG. 10A has reflection symmetry with respect to, for example, axis 1010 and point/rotational symmetry with respect to, for example, point 1015. Similarly, it can be seen that a physical instance of the unit cell (and thus a combination of physical instances of the unit cell) in FIG. 10C has a geometric symmetry.

In an embodiment, the unit cell has a geometric symmetry for a certain feature (such as overlay). Embodiments herein focus on the unit cell having zero overlay when it is geometrically symmetric. However, instead, the unit cell can have zero overlay for a certain geometric asymmetry. Appropriate offsets and calculations would then be used to account for the unit cell having a zero overlay when it has a certain geometric asymmetry. Pertinently, the unit cell should be capable of change in symmetry (e.g., become asymmetric, or become further asymmetric, or become symmetric from an asymmetric situation) depending on the certain feature value.

In the example of FIG. 10A, the unit cell has a geometric symmetry for a zero overlay (although it need not be zero overlay). This is represented by the arrows 1020 and 1025 which shows that the lines of the first structure 1000 are evenly aligned with respect to the oval-type shape of the second structure 1005 (and which even alignment at least in part enables the unit cell to have geometric symmetry as shown in FIG. 10A). So, in this example, when the unit cell has geometric symmetry, there is zero overlay. However, when there is an error in overlay (e.g., a non-zero overlay), the unit cell is no longer geometrically symmetric and by definition the target is no longer geometrically symmetric.

Further, where a target comprises a plurality of physical instances of the unit, the instances of the unit cell are arranged periodically. In an embodiment, the instances of the unit cell are arranged in a lattice. In an embodiment, the periodic arrangement has a geometric symmetry within the target.

So, in this technique, as discussed further hereafter, advantage is taken of the change in geometric symmetry (e.g., a change to a geometric asymmetry, or change to a further geometric asymmetry, or a change from geometric asymmetry to geometric symmetry) related to a feature asymmetry of interest (e.g., non-zero overlay) to be able to determine the feature asymmetry (e.g., non-zero overlay).

A target comprising a physical instance of the unit cell of FIG. 10A can be illuminated with radiation using, for example, the metrology apparatus of FIG. 7. The radiation redirected by the target can be measured, e.g., by detector 190. In an embodiment, a pupil of the redirected radiation is measured, i.e., a Fourier transform plane. An example measurement of such a pupil is depicted as pupil image 1030. While the pupil image 1030 has a diamond-type shape, it need not have such a shape. The term pupil and pupil plane herein includes any conjugates thereof unless the context otherwise requires (for example, where a pupil plane of a particular optical system is being identified). The pupil image 1030 is effectively an image, specified in terms of an optical characteristic (in this case intensity), of a pupil of the redirected radiation.

For convenience, the discussion herein will focus on intensity as an optical characteristic of interest. But, the techniques herein may be used with one or more alternative or additional optical characteristics, such as phase and/or reflectivity.

Further, for convenience, the discussion herein focuses on detecting and processing images of redirected radiation and in particular pupil images. However, the optical properties of the redirected radiation can be measured and represented in different manners than images. For example, the redirected radiation can be processed in terms of one or more spectrums (e.g., intensity as a function of wavelength). Thus, a detected image of redirected radiation can be considered as an example of an optical representation of the redirected radiation. So, in the case of a pupil plane image, a pupil image is an example of a pupil representation.

Further, the redirected radiation can be polarized or non-polarized. In an embodiment, the measurement beam radiation is polarized radiation. In an embodiment, the measurement beam radiation is linearly polarized.

In an embodiment, a pupil representation is of primarily, or substantially, one diffraction order of redirected radiation from the target. For example, the radiation can be 80% or more, 85% or more, 90% or more, 95% or more, 98% or more or 99% or more, of a particular order of the radiation. In an embodiment, the pupil representation is of primarily, or substantially, zeroth order redirected radiation. This can occur, for example, when the pitch of the target, the wavelength of the measurement radiation, and optionally one or more other conditions cause the target to redirect primarily zeroth order (although there can be radiation of one or more higher orders). In an embodiment, a majority of the pupil representation is zeroth order redirected radiation. In an embodiment, the pupil representation is of zeroth radiation and separately of $1^{st}$ order radiation, which can then be linearly combined (superposition). The aperture 186 in FIG. 7 can be used to select a particular order, e.g., the zeroth order, of radiation.

Having regard to pupil image 1030 corresponding to the geometrically symmetric unit cell of the first and second structures 1000, 1005, it can be seen that the intensity distribution is essentially symmetric within the pupil image (e.g., with the same symmetry type as of the geometric structure). This is further confirmed by removing the symmetric intensity distribution portion from the pupil image 1030, which results in the derived pupil image 1035. To remove the symmetric intensity distribution portion, a particular pupil image pixel (e.g., a pixel) can have the symmetric intensity distribution portion removed by subtracting from the intensity at that particular pupil image pixel the intensity of a symmetrically located pupil image pixel, and vice versa. In an embodiment, the pixel can correspond to the pixels of the detector (e.g., detector 190), but it need not; for example, a pupil image pixel could be a plurality of the pixels of the detector. In an embodiment, the point or axis of symmetry across which pixel intensities are subtracted corresponds with a point or axis of symmetry of the unit cell. So, for example, considering pupil image 1030, the symmetry intensity distribution portion can be removed by, for example, subtracting from the intensity $I_i$ at that particular pixel shown the intensity $I_i'$ from a symmetrically located pixel, i.e., symmetrically located with respect to axis 1032. Thus, the intensity at a particular pixel with the symmetrical intensity portion removed, $S_i$, is then $S_i=I_i-I_i'$. This can be repeated for a plurality of pixels of the pupil image, e.g., all the pixels in the pupil image. As seen in the derived pupil image 1035, the intensity distribution corresponding to the symmetric unit cell is essentially completely symmetric. Thus, a symmetric target with a symmetric unit cell geometry (and if applicable, a certain periodicity of instances of the unit cell) results in a symmetric pupil response as measured by a metrology apparatus.

Referring now to FIG. 10B, an example of an error in overlay is depicted with respect to the unit cell depicted in FIG. 10A. In this case, the first structure 1000 is shifted in the X-direction with respect to the second structure 1005. In particular, the axis 1010 centered on the lines of the first structure 1000 has shifted to the right in FIG. 10B to axis 1045. Thus, there is an error in the overlay 1040 in the X-direction; that is, an X direction overlay error. Of course, the second structure 1005 could be shifted relative to the first structure 1000 or both could be shifted relative to each other. In any event, the result is an X direction overlay error. However, as should be appreciated from this unit cell arrangement, a purely relative shift in the Y-direction between the first structure 1000 and the second structure 1005 would not change the geometric symmetry of this unit cell. But, with an appropriate geometric arrangement, overlay in two directions or between different combinations of parts of the unit cell can change symmetry and could also be determined, as further discussed below.

As a consequence of the change in the physical configuration of the unit cell from the nominal physical configuration of the unit cell in FIG. 10A and represented by the error in overlay 1040, the result is that the unit cell has become geometrically asymmetric. This can be seen by the arrows 1050 and 1055 of different length, which show that the oval-type shape of the second structure 1005 is unevenly located relative to the lines of the first structure 1000. The symmetry is examined with respect to the point or axis of symmetry of the pupil image 1030, i.e. in that case, axis 1032 which is now shown axis 1034.

The physical instance of the unit cell of FIG. 10B can be illuminated with radiation using, for example, the metrology apparatus of FIG. 7. A pupil image of the redirected radiation can be recorded, e.g., by detector 190. An example of such a pupil image is depicted as pupil image 1060. The pupil image 1060 is effectively an image of the intensity. While the pupil image 1060 has a diamond-type shape, it need not have such a shape; it can be a circular shape or any other shape. Moreover, the pupil image 1060 is of a substantially same axis or coordinate location as pupil image 1030. That is, in this embodiment, an axis of symmetry 1010 in the unit cell of FIG. 10A and the same axis in the unit cell of FIG. 10B align with an axis of symmetry 1032 of the pupil images 1030, 1060.

Having regard to pupil image 1060 corresponding to the geometrically asymmetric unit cell of the first and second structures 1000, 1005, it visually seems like the intensity distribution is essentially symmetric within the pupil image. However, there is an asymmetric intensity distribution portion within the pupil image. This asymmetric intensity distribution portion is due to the asymmetry in the unit cell. Moreover, the asymmetric intensity distribution is significantly lower in magnitude than a symmetric intensity distribution portion in the pupil image.

So, in an embodiment, to more effectively isolate the asymmetric intensity distribution portion, the symmetric intensity distribution portion can be removed from the pupil image 1060, which results in the derived pupil image 1065. Like with obtaining derived pupil image 1035, a particular pupil image pixel (e.g., a pixel) can have the symmetric intensity distribution portion removed by subtracting from the intensity at that particular pupil image pixel the intensity of a symmetrically located pupil image pixel, and vice versa, as discussed above. So, for example, considering pupil image 1060, the symmetry intensity distribution portion can be removed by, for example, subtracting from the intensity $I_i$ at that particular pixel shown the intensity $I_i'$ from a symmetrically located pixel, i.e., symmetrically located with respect to axis 1032 to yield $S_i$. This can be repeated for a plurality of pixels of the pupil image, e.g., all the pixels in the pupil image. In FIGS. 10A and 10B, the full derived pupil images of $S_i$ are depicted for explanation purposes. As will be appreciated, half of a derived pupil image of FIG. 10A or 10B is the same as the other half thereof. So, in an embodiment, the values from only half of the pupil image can be used for further processing discussed herein and so a derived image pupil used in further processing herein can be only half of the $S_i$ values for a pupil.

As seen in the derived pupil image 1065, the intensity distribution measured using a physical instance of an asymmetric unit cell is not symmetric. As seen in regions 1075 and 1080, there is an asymmetric intensity distribution portion visible once the symmetric intensity distribution portion is removed. As noted above, the full derived pupil image 1065 is shown and so the asymmetric intensity distribution portion is shown on both halves (even though they are equal to each other in terms of magnitude and distribution in their respective halves).

Thus, an asymmetry in the geometrical domain corresponds to an asymmetry in the pupil. So, in an embodiment, a method is provided that uses the optical response of a periodic target that possesses, or is capable of, inherent geometric symmetry in its physical instance of a unit cell to determine a parameter corresponding to a physical configuration change that causes a change in geometric symmetry (e.g., cause an asymmetry, or cause a further asymmetry, or cause an asymmetric unit cell to become symmetric) of the physical instance of the unit cell. In particular, in an embodiment, an overlay induced asymmetry (or lack thereof) in the pupil as measured by a metrology apparatus can be exploited to determine the overlay. That is, the pupil asymmetry is used to measure the overlay within the physical instance of the unit cell and thus within the target.

The change in symmetry in the geometrical domain of the target T can arise due to a relative shift between first and second structures 1000, 1005 from their expected positioning. The relative shift may occur due to an error in overlay between a patterning process used to form the first structure 1000 and a patterning process used to form the second structure 1005.

In a regime where a metric characterizing a component of a detected pupil representation (e.g. a metric measuring a strength of asymmetry in a pupil image, as discussed above) varies linearly with the parameter of interest (e.g. overlay), there will be an unambiguous one-to-one relationship between the metric and the parameter of interest. The one-to-one relationship means that a unique inverse mapping can be performed from an observed signal (that provides a value for the metric) to a parameter of interest (that influences the observed signal).

However, as features of interest become smaller and/or it is desirable to use longer measuring wavelengths, the linear relationship between measured metric and parameter of interest may be lost. This may also occur where higher harmonics of the target stack become dominant. In some cases, the measured metric may even vary in a non-monotonic manner within a range of interest for the parameter of interest. The non-monotonic variation may lead to a situation where plural values of a parameter of interest all correspond to a single obtained value of the metric. Parameters of interest such as overlay and target stack height variation may be expected to yield non-monotonic periodic signals, for example. An example of such a situation is depicted in FIG. 11.

Figure 11:
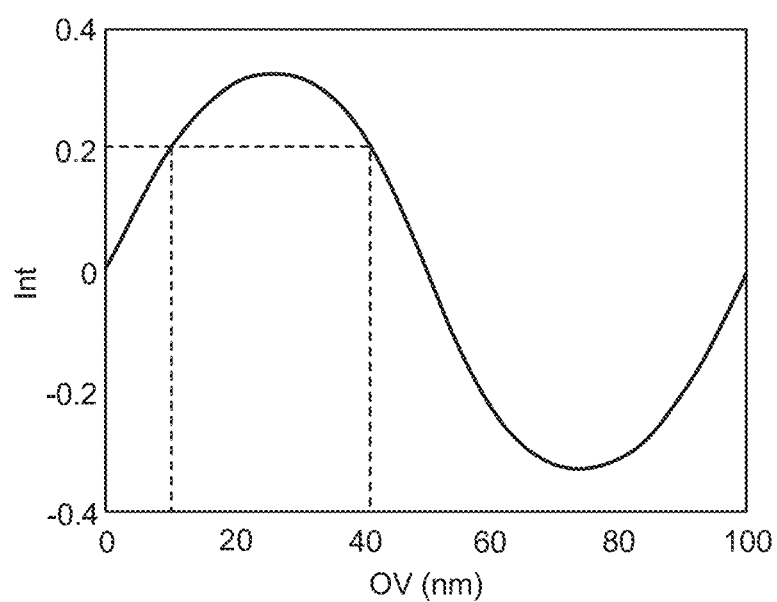
FIG. 11 is a graph schematically depicting an expected variation of a metric of an asymmetric component of a detected pupil representation as a function of a value of a parameter of interest.

FIG. 11 schematically depicts variation of a metric (in this case, a signal intensity Int) characterizing an asymmetric component of a detected pupil representation as a function of a parameter of interest OV (e.g. overlay). In this example, a value of the metric is zero (e.g. representing no asymmetry in the detected pupil representation) when the value of the parameter of interest is zero (e.g. when there is no overlay error). As the value of the parameter of interest increases (e.g. as an overlay error increases), the value of the metric initially increases approximately linearly. As the value of the parameter of interest increases further, however, the value of metric starts to vary non-monotonically, in this case approximately sinusoidally. It can be seen from the variation that if a measurement of the metric yields a value of 0.2, for example, there is some uncertainty (as indicated by the broken lines) about whether the value of the parameter of interest corresponding to this measured value of the metric is about 10 nm or about 40 nm. The following embodiments of the disclosure aim to overcome this uncertainty and allow an accurate and reliable value of the parameter of interest to be obtained.

Figure 12:
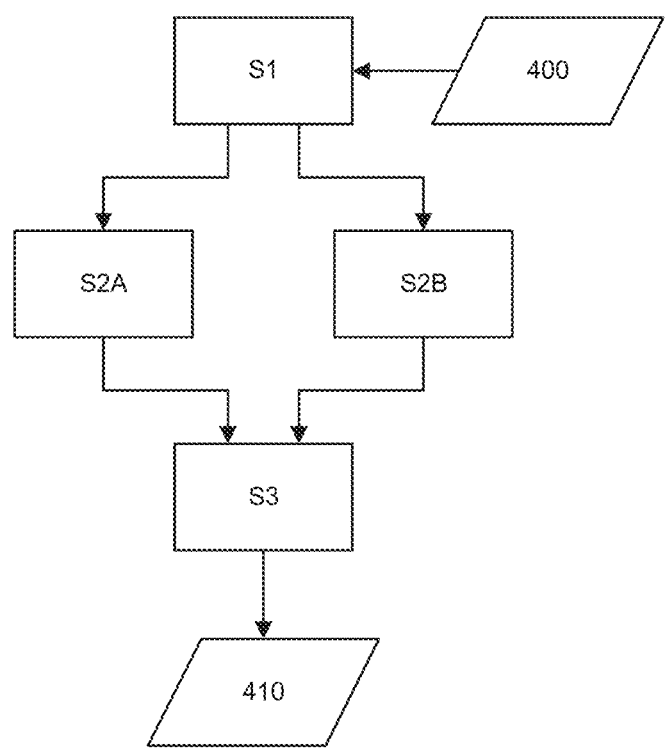
FIG. 12 depicts a flow chart describing a method for determining a value of a parameter of interest according to an embodiment.

FIG. 12 depicts an example framework for a method of determining a value of a parameter of interest of a target formed by a patterning process on a substrate.

Measurement data 400 is provided to step S1. The measurement data 400 represents the result of applying a measurement process to a target on a substrate. In an embodiment, the measurement process comprises illuminating the target with radiation and detecting radiation redirected (e.g. scattered) by the target. The measurement process may be performed by any of the metrology apparatuses described above. In some embodiments, the measurement process (which may also be referred to as a metrology process) is performed by directing radiation onto a target and detecting a representation of the redirected radiation as described above with reference to FIGS. 7-10C. The detected representation of radiation may comprise a detected pupil representation of an optical characteristic of radiation in a pupil plane, as described above with reference to FIGS. 7-10C. The optical characteristic may comprise a radiation intensity or phase. In the case where the optical characteristic comprises a radiation intensity, the detected pupil representation may be referred to as a pupil image. A metrology apparatus of the type described with reference to FIG. 7 may be used for example to perform the metrology process. The detected representation of radiation may comprise primarily zeroth order radiation, as described above. This may be particularly desirable where the target comprises a high-resolution target, such as a device structure. Thus, in an embodiment, the target comprises a device structure. In other embodiments, the target comprises a non-device structure within a substrate die comprising a device structure.

Step S1 comprises deriving both a symmetric component of the detected pupil representation and an asymmetric component of the detected pupil representation. In some embodiments, either or both of the symmetric component and the asymmetric component is/are derived as described above with reference to FIGS. 10A and 10B. Thus, a derived pupil image representing an asymmetric component, such as the derived pupil image 1035 or 1065 of FIGS. 10A or 10B may be obtained, or a corresponding derived pupil image representing a symmetric component may be obtained, or both may be used. In an embodiment, the asymmetric component and the symmetric component together contain all information present in the detected pupil representation. In an embodiment, the asymmetric component is obtained by anti-symmetrizing the detected pupil representation. In an embodiment, anti-symmetrization of the detected pupil representation comprises removing the symmetric component of the detected pupil representation. In an embodiment, the symmetric component of the detected pupil representation is removed as described above with reference to FIGS. 10A and 10B. Considering pupil image 1030, the symmetric component can be removed by, for example, subtracting from the intensity $I_i$ at that particular pixel shown the intensity $I_i'$ from a symmetrically located pixel, i.e., symmetrically located with respect to axis 1032. Thus, the intensity at a particular pixel with the symmetrical intensity portion removed, $S_i$, is then $S_i=I_i-I_i'$. This can be repeated for a plurality of pixels of the detected pupil presentation, e.g., all the pixels in the detected pupil representation, to obtain an asymmetric component of the detected pupil representation. A corresponding process can be performed to obtain the symmetric component of the detected pupil representation.

In an embodiment, the symmetric component is point symmetric (e.g. symmetric with respect to reflection relative to a point) with respect to a reference point in the pupil plane. The point symmetry may correspond to a point symmetry in a target unit cell, as described above with reference to FIGS. 10A and 10B (see, e.g., point 1015 in FIG. 10A). In an embodiment, the symmetric component is mirror symmetric with respect to a reference line in the pupil plane. This symmetry may correspond to a mirror symmetry with respect to a corresponding line in a target unit cell, as described above with reference to FIGS. 10A and 10B (see, e.g., axis 1010).

In an embodiment, the asymmetric component is point asymmetric with respect to a reference point in the pupil plane. The point asymmetry may correspond to a deviation from a point symmetry in a target unit cell, as described above with reference to FIGS. 10A and 10B. In an embodiment, the asymmetric component is mirror asymmetric with respect to a reference line in the pupil plane. This asymmetry may correspond to a deviation from a mirror symmetry with respect to a reference line in a target unit cell, as described above with reference to FIGS. 10A and 10B.

In an embodiment, a first metric is used to characterize the symmetric component. The first metric may for example provide a measure of the relative strength of the symmetric component in the detected pupil representation. The first metric may be derived, for example, from a sum (optionally a weighted sum) of intensities of pixels in a symmetrized version of the detected pupil representation.

In an embodiment, a second metric is used to characterize the asymmetric component. The second metric may for example provide a measure of the relative strength of the asymmetric component in the detected pupil representation. The second metric may be derived, for example, from a sum (optionally a weighted sum) of intensities of pixels in an anti-symmetrized version of the detected pupil representation.

The target type and the measurement process are such that the first metric and the second metric both vary non-monotonically (e.g. as depicted in FIG. 11 or a phase-shifted version thereof) as a function of a parameter of interest over a reference range of values of the parameter of interest. In some embodiments, the reference range of values represents a range expected to be encountered under typical variations of the parameter of interest between instances of the target formed at different locations on the substrate and/or at different times, due to variations in the patterning process or patterning processes used to form the targets.

According to an embodiment, the first metric is derived in step S2A and the second metric is derived in step S2B. The derived first metric and the derived second metric are provided to step S3.

In step S3, a combination of the derived symmetric component (e.g. the first metric) and the derived asymmetric component (e.g. the second metric) are used to identify a correct value from a plurality of candidate values of the parameter of interest. The correct value is output as output data 410. Thus, in the particular example of FIG. 11, step S3 of the method of FIG. 12 can be used to determine which of the two candidate values (10 nm or 40 nm) for the parameter of interest corresponding to the obtained metric value of 0.2 is the correct value. The combination of the derived symmetric component and the derived asymmetric component can be used to identify a correct value from a plurality of candidate values of the parameter of interest that all correspond, due to the non-monotonic variation of the first metric, to a value of the first metric corresponding to the derived symmetric component for the target. Alternatively or additionally, the combination of the derived symmetric component and the derived asymmetric component can be used to identify a correct value from a plurality of candidate values of the parameter of interest that all correspond, due to the non-monotonic variation of the second metric, to a value of the second metric corresponding to the derived asymmetric component for the target (as in FIG. 11). In essence, an ambiguity in a value of the parameter of interest obtained from one of the symmetric component and the asymmetric component can be resolved efficiently by using information derived from the other of the symmetric component and the asymmetric component. The parameter of interest may comprise any of the following: a measure of an asymmetry in the target, overlay, side wall angle asymmetry, critical dimension, and/or stack height variation. Specific examples of how this can be achieved are described below.

Figure 13:
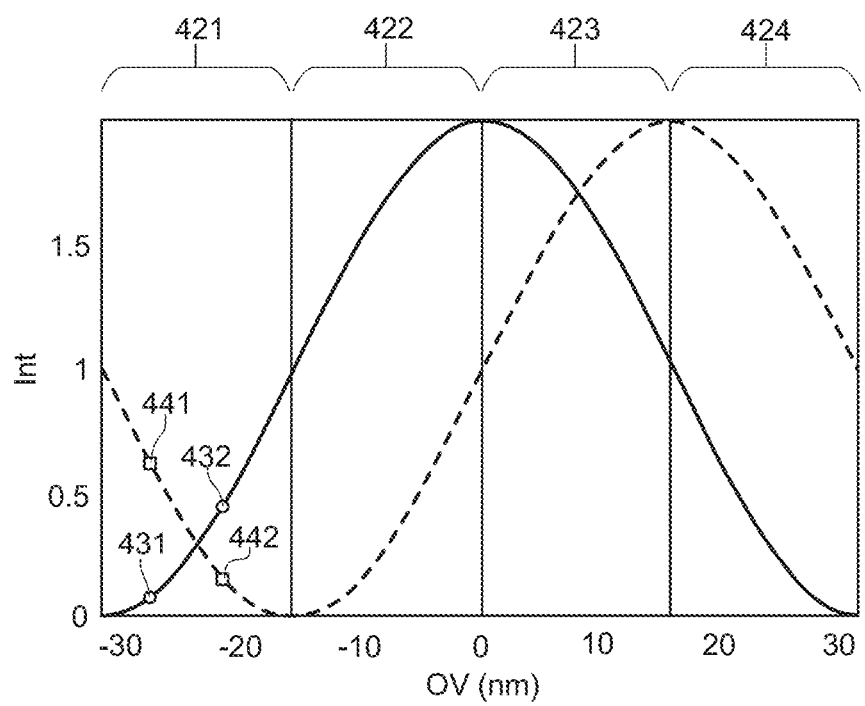
FIG. 13 is a graph schematically depicting an expected variation of a first metric of a symmetric component of a detected pupil representation and of a second metric of an asymmetric component of a detected pupil representation, as a function of a value of a parameter of interest within four quadrants of a periodic variation.

In an embodiment, the non-monotonic variation of the first metric and/or the second metric is at least approximately a periodic variation. An example of one period of such a variation is depicted in FIG. 13. The solid line represents variation of the first metric (represented as an intensity level, Int) as a function of the parameter of interest (e.g. overlay, OV). The broken line represents variation of a second metric as a function of the same parameter of interest.

In an embodiment, the reference range of values of the parameter of interest corresponds to one period of the periodic variation (as depicted in FIG. 13).

In an embodiment, the periodic variation of the first metric has the same period as the periodic variation of the second metric (as depicted in FIG. 13).

In an embodiment, the periodic variation of the first metric is phase shifted relative to the periodic variation of the second metric. In an embodiment, the phase shift is 90 degrees (as depicted in FIG. 13). This would be the case, for example, where the parameter of interest represents an asymmetry in the target such as an error in overlay.

In an embodiment, the periodic variation is at least approximately sinusoidal (as depicted in FIG. 13).

In an embodiment, one period of the periodic variation can be divided into four quadrants of equal size (i.e. each a quarter of the period). Examples of such quadrants 421-424 are depicted in FIG. 13. The quadrants may be positioned so as to each extend between a point of inflexion and a turning point (i.e. local maximum or local minimum) of the periodic variation.

In an embodiment, in step S1 of FIG. 12, the symmetric component and the asymmetric component are derived for each of a set of detected pupil representations obtained from a corresponding set of targets. In an embodiment, the set of targets are located in close proximity to each other so as to have similar values of the parameter of interest. Thus, for example, the targets in the set that are furthest apart from each other may each be separated from at least one other target that is not in the set by a larger amount.

In an embodiment, step S2A comprises deriving the first metric of the symmetric component for each target in the set of targets and using the resulting derived first metrics and corresponding values of the parameter of interest to estimate at least a sign of a rate of change of the first metric with respect to the value of the parameter of interest in a sub-region of the reference range. An example of this process for two targets is depicted in FIG. 13. A first metric and a value of the parameter of interest are plotted for the first target at position 431. A first metric and a value of the parameter of interest are plotted for the second target at position 432. An estimate of the rate of change of the first metric in a sub-region of the reference range can be obtained in this example by interpolating between the two plotted points. The gradient of the resulting line approximates the gradient of the curve of the first metric against the parameter of interest. The sign of the gradient is positive in this example.

In an embodiment, step S2B comprises deriving the second metric of the asymmetric component for each target in the set of targets and using the resulting derived second metrics and corresponding values of the parameter of interest to estimate at least a sign of a rate of change of the second metric with respect to the value of the parameter of interest in a sub-region of the reference range. An example of this process for two targets is depicted in FIG. 13. A second metric and a value of the parameter of interest are plotted for the first target at position 441. A second metric and a value of the parameter of interest are plotted for the second target at position 442. An estimate of the rate of change of the second metric in a sub-region of the reference range can be obtained in this example by interpolating between the two plotted points. The gradient of the resulting line approximates the gradient of the curve of the second metric against the parameter of interest. The sign of the gradient is negative in this example.

In an embodiment, the sign of the rate of change of the first metric determined in step S2A and the sign of the rate of change of the second metric determined in step S2B are used to identify where in the reference range the sub-region is located (e.g. which of the quadrants 421-424). Ambiguity about the correct value of the parameter of interest can therefore be resolved.

In examples of the type described above with reference to FIG. 13 in which the non-monotonic variation is at least approximately a periodic variation, and the reference range of values of the parameter of interest corresponds to one period of the periodic variation having four quadrants, the location of the sub-region can be identified as follows. When the rate of change of the first metric is positive and the rate of change of the second metric is negative, it is determined that the sub-region is located in a first 421 of the four quadrants. When the rate of change of the first metric is positive and the rate of change of the second metric is positive, it is determined that the sub-region is located in a second 422 of the four quadrants. When the rate of change of the first metric is negative and the rate of change of the second metric is positive, it is determined that the sub-region is located in a third 423 of the four quadrants. When the rate of change of the first metric is negative and the rate of change of the second metric is negative, it is determined that the sub-region is located in a fourth 424 of the four quadrants.

Figure 14:
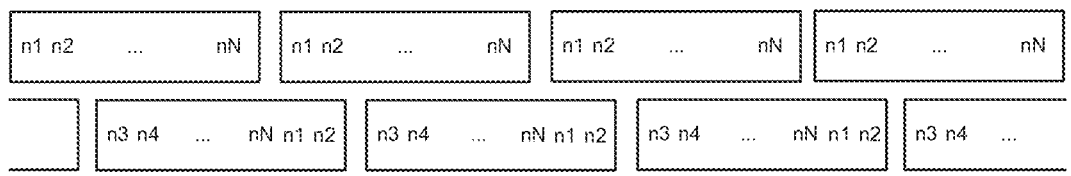
FIG. 14 depicts alternative target sampling schemes for a data driven method according to an embodiment.

In an embodiment, the targets in the set of targets are selected such that the value of the parameter of interest is in the same quadrant of the reference range for all of the targets in the set. This can be achieved by selecting targets that are located close together on the substrate, such that the value of the parameter of interest will be similar for each of the targets in the set. In this way, the set of targets will together only sample a relatively small proportion of the total period of the periodic variation. This increases the chance that all of the targets in the set will be in the same quadrant. Where it is found that some of the targets in a given set belong to different quadrants, sampling of the targets may be altered until all of the targets in each set do belong in the same quadrant. FIG. 14 depicts schematically how this could be achieved. Each rectangle in the upper series of rectangles represents a different sampled set of N targets, n1, n2, . . . nN. The sampling of the sets can be altered as needed, for example, by using a sliding window to change the population of the sets. This is depicted schematically in the lower series of rectangles, which divide the targets into sets differently than in the upper series of rectangles. In an embodiment, the set of targets may also be selected so as to be in a region sufficiently far away from a turning point in the variation of the periodic variation to achieve high sensitivity.

The above-described approach of using multiple targets to establish a location of a sub-region of the reference range in which the value of the parameter of interest must be located may be referred to as a data driven approach. In an additional or alternative embodiment, which may be referred to as a model driven approach, a mathematical model is used to address the same problem and allows the location of the sub-region to be determined without necessarily requiring measurements from multiple different targets to be used.

Figure 15:
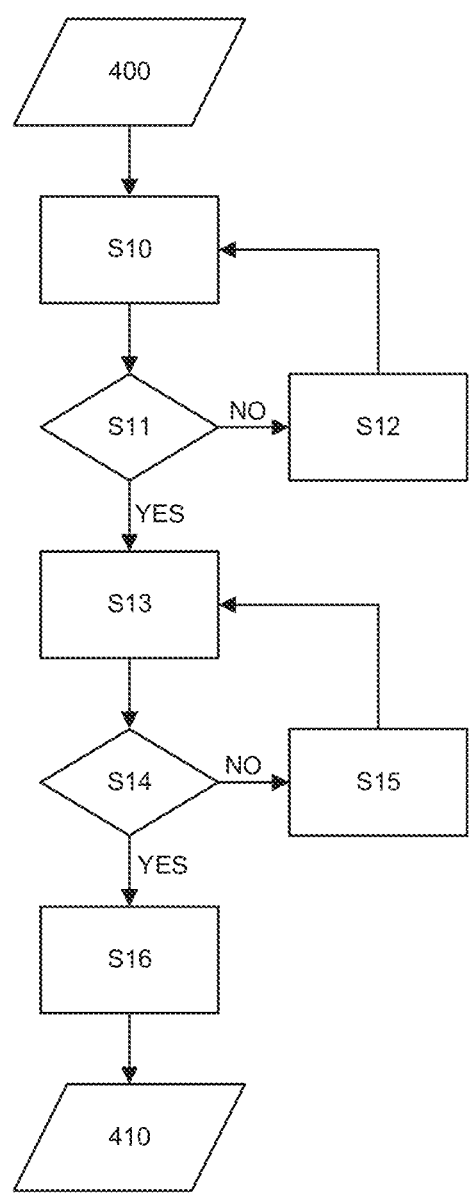
FIG. 15 depicts a flow chart describing an example of a model driven approach for determining a value of a parameter of interest according to an embodiment.
Figure 16:
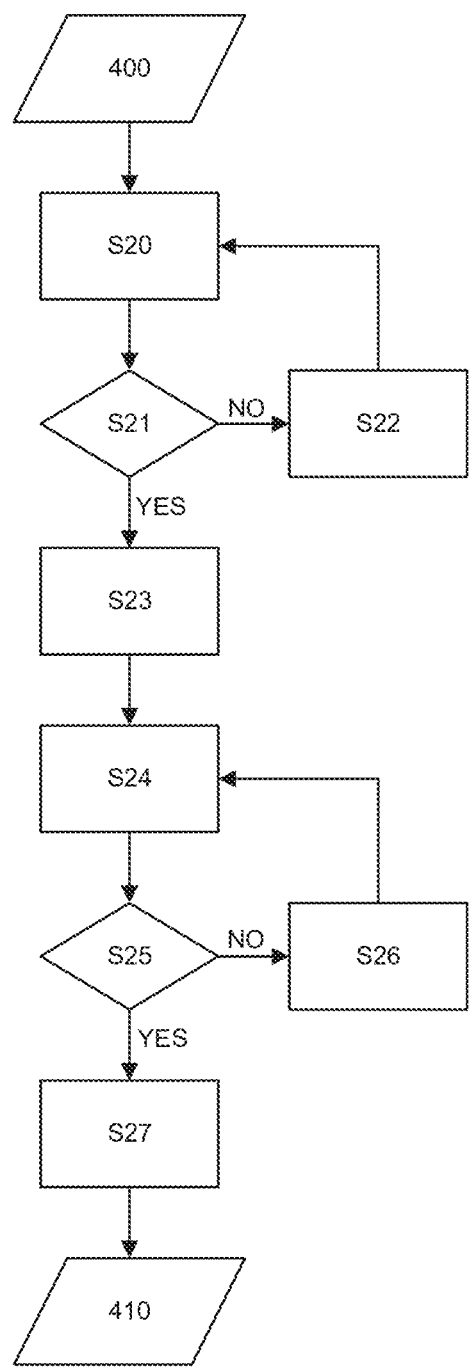
FIG. 16 depicts a flow chart describing an example of a model driven approach for determining a value of a parameter of interest according to an embodiment.
Figure 17:
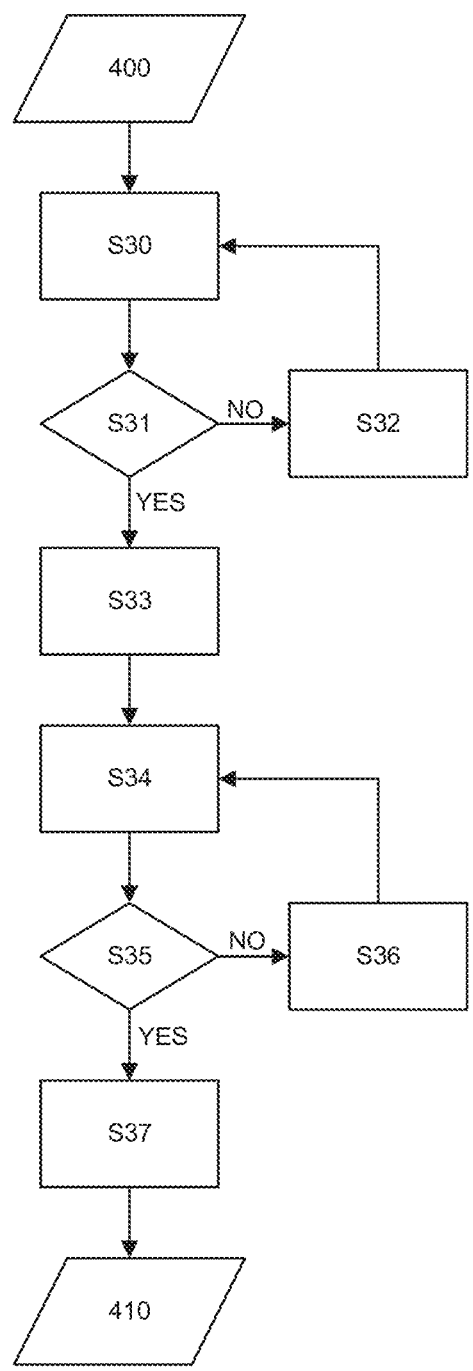
FIG. 17 depicts a flow chart describing an example of a model driven approach for determining a value of a parameter of interest according to an embodiment.

Three examples of the model-driven approach are respectively depicted schematically in FIGS. 15-17.

In the example of FIG. 15, measurement data 400 is provided to step S10. The measurement data 400 may take any of the forms described above with reference to FIG. 12. In step S10, a first fitting process is performed. The first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized. The fitting process and mathematical model may take any of the forms described above with reference to FIG. 9. A numerical Maxwell solver 210 may be used, for example, to compute/simulate a radiation distribution 208 from a parameterized mathematical model 206. The one or more parameters include the parameter of interest. The first fitting process is repeated a plurality of times through loop S11 and S12. Each time the first fitting process is performed, the first fitting process is initiated with a value of the parameter of interest in a different one of a plurality of sub-regions of the reference range, for example in a different quadrant of the reference range. Step S11 queries whether the first fitting process has been initiated in all required sub-regions. If NO, the sub-region is changed in step S12 and the first fitting process is repeated in step S10. If YES, the process proceeds to step S13.

In step S13, a second fitting process is performed. The second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized. The fitting process and mathematical model may take any of the forms described above with reference to FIG. 9. A numerical Maxwell solver 210 may be used, for example, to compute/simulate a radiation distribution 208 from a parameterized mathematical model 206. The one or more parameters include the parameter of interest. The second fitting process is repeated a plurality of times through loop S14 and S15 in a similar way to the first fitting process (through S11 and S12). Each time the second fitting process is performed, the second fitting process is initiated with a value of the parameter of interest in a different one of the plurality of sub-regions of the reference range, for example in a different quadrant of the reference range. When all required performances of the second fitting process have been completed, the process proceeds to step S16.

In step S16, the minimized fitting errors obtained by either or both of the first fitting process in different respective sub-regions and the second fitting process in different respective sub-regions are used to identify the sub-region in which the correct value of the parameter of interest is located. In an embodiment, this is achieved by identifying the sub-region in which the minimized fitting errors are below a predetermined threshold for both of the first fitting process and the second fitting process. A correct value of the parameter of interest is output as output data 410.

FIG. 16 depicts an example process which reduces processing requirements by using results from a plurality of applications of the first fitting process to select a subset of the sub-regions for further consideration in a subsequent plurality of applications of the second fitting process.

In the example of FIG. 16, measurement data 400 is provided to step S20. The measurement data 400 may take any of the forms described above with reference to FIG. 12. Steps S20, S21 and S22 are the same as steps S10, S11 and S12 of FIG. 15. Each performance of the first fitting process in the loop S20, S21 and S22 yields a fitted value of the parameter of interest when the fitting error is minimized.

In step 23, a subset of the sub-regions is selected. Each sub-region in the subset is a sub-region in which the minimized fitting error obtained by the first fitting process is lower than the minimized fitting error obtained by the first fitting process in all sub-regions not in the subset. Thus, some of the sub-regions are rejected at this stage on the basis that the minimized fitting error is too large in comparison to the minimized fitting error achieved for other sub-regions.

In steps S24-S26, the second fitting process is performed a plurality of times in a similar manner to in steps S13-S15 of FIG. 15, except that in this embodiment each performance of the second fitting process is initiated with a different one of the fitted values of the parameter of interest obtained by the performance of the first fitting process in each sub-region of the selected subset of sub-regions. A fitted value of the parameter of interest is obtained for each performance of the second fitting process.

In step S27, the fitted value of the parameter of interest with the lowest minimized fitting error output from steps S24-26 is output as output data 410 representing the correct value of the parameter of interest.

In one particular implementation of the embodiment of FIG. 16 in which the non-monotonic variation is at least approximately a periodic variation, and the reference range of values of the parameter of interest corresponds to one period of the periodic variation having four quadrants, the method proceeds as follows. The sub-regions in which the first fitting process is performed in steps S20-22 comprise: a first sub-region consisting of a first 421 of the quadrants; a second sub-region consisting of a second of the quadrants 422 and a third of the quadrants 423; and a third sub-region consisting of a fourth 424 of the quadrants. The subset of the sub-regions selected in step S23 consists of two selected from: the first sub-region 421, second sub-region 422 or 423, and third sub-region 424.

FIG. 17 depicts a variation on the embodiment of FIG. 16 in which the second fitting processes are performed before the first fitting processes.

In the example of FIG. 17, measurement data 400 is provided to step S30. The measurement data 400 may take any of the forms described above with reference to FIG. 12. Steps S30, S31 and S32 are the same as steps S10, S11 and S12 of FIG. 15 except that the second fitting process is used instead of the first fitting process. Each performance of the second fitting process in the loop S30, S31 and S32 yields a fitted value of the parameter of interest when the fitting error is minimized.

In step 33, a subset of the sub-regions is selected. Each sub-region in the subset is a sub-region in which the minimized fitting error obtained by the second fitting process is lower than the minimized fitting error obtained by the second fitting process in all sub-regions not in the subset. Thus, some of the sub-regions are rejected at this stage on the basis that the minimized fitting error is too large in comparison to the minimized fitting error achieved for other sub-regions.

In steps S34-S36, the first fitting process is performed a plurality of times in a similar manner to in steps S13-S15 of FIG. 15, except that in this embodiment the first fitting process is being performed and each performance of the first fitting process is initiated with a different one of the fitted values of the parameter of interest obtained by the performance of the second fitting process in each sub-region of the selected subset of sub-regions. A fitted value of the parameter of interest is obtained for each performance of the first fitting process.

In step S37, the fitted value of the parameter of interest with the lowest minimized fitting error output from steps S34-36 is output as output data 410 representing the correct value of the parameter of interest.

Figure 18:
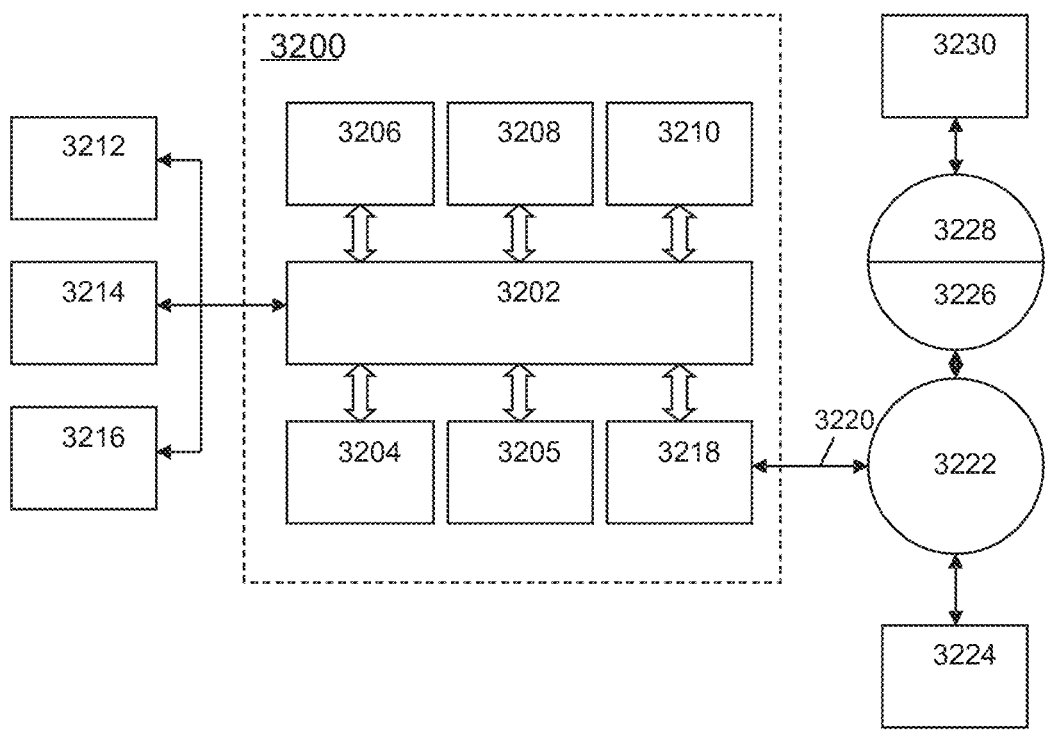
FIG. 18 depicts a computer system which may implement embodiments of the disclosure.

Referring to FIG. 18, a computer system 3200 is shown. The computer system 3200 includes a bus 3202 or other communication mechanism for communicating information, and a processor 3204 (or multiple processors 3204 and 3205) coupled with bus 3202 for processing information.

Computer system 3200 also includes a main memory 3206, such as a random-access memory (RAM) or other dynamic storage device, coupled to bus 3202 for storing information and instructions to be executed by processor 3204. Main memory 3206 also may be used for storing temporary variables or other intermediate information during execution of instructions to be executed by processor 3204. Computer system 3200 further includes a read only memory (ROM) 3208 or other static storage device coupled to bus 3202 for storing static information and instructions for processor 3204. A storage device 3210, such as a magnetic disk or optical disk, is provided and coupled to bus 3202 for storing information and instructions.

Computer system 3200 may be coupled via bus 3202 to a display 3212, such as a cathode ray tube (CRT) or flat panel or touch panel display for displaying information to a computer user. An input device 3214, including alphanumeric and other keys, is coupled to bus 3202 for communicating information and command selections to processor 3204. Another type of user input device is cursor control 3216, such as a mouse, a trackball, or cursor direction keys for communicating direction information and command selections to processor 3204 and for controlling cursor movement on display 3212. This input device typically has two degrees of freedom in two axes, a first axis (e.g., x) and a second axis (e.g., y), that allows the device to specify positions in a plane. A touch panel (screen) display may also be used as an input device.

The computer system 3200 may be suitable to function as a processing unit herein in response to processor 3204 executing one or more sequences of one or more instructions contained in main memory 3206. Such instructions may be read into main memory 3206 from another computer-readable medium, such as storage device 3210. Execution of the sequences of instructions contained in main memory 3206 causes processor 3204 to perform a process described herein. One or more processors in a multi-processing arrangement may also be employed to execute the sequences of instructions contained in main memory 3206. In alternative embodiments, hard-wired circuitry may be used in place of or in combination with software instructions. Thus, embodiments are not limited to any specific combination of hardware circuitry and software.

The term "computer-readable medium" as used herein refers to any medium that participates in providing instructions to processor 3204 for execution. Such a medium may take many forms, including but not limited to, non-volatile media, volatile media, and transmission media. Non-volatile media include, for example, optical or magnetic disks, such as storage device 3210. Volatile media include dynamic memory, such as main memory 3206. Transmission media include coaxial cables, copper wire and fiber optics, including the wires that comprise bus 3202. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 3204 for execution. For example, the instructions may initially be borne on a magnetic disk of a remote computer. The remote computer can load the instructions into its dynamic memory and send the instructions over a telephone line using a modem. A modem local to computer system 3200 can receive the data on the telephone line and use an infrared transmitter to convert the data to an infrared signal. An infrared detector coupled to bus 3202 can receive the data carried in the infrared signal and place the data on bus 3202. Bus 3202 carries the data to main memory 3206, from which processor 3204 retrieves and executes the instructions. The instructions received by main memory 3206 may optionally be stored on storage device 3210 either before or after execution by processor 3204.

Computer system 3200 may also include a communication interface 3218 coupled to bus 3202. Communication interface 3218 provides a two-way data communication coupling to a network link 3220 that is connected to a local network 3222. For example, communication interface 3218 may be an integrated services digital network (ISDN) card or a modem to provide a data communication connection to a corresponding type of telephone line. As another example, communication interface 3218 may be a local area network (LAN) card to provide a data communication connection to a compatible LAN. Wireless links may also be implemented. In any such implementation, communication interface 3218 sends and receives electrical, electromagnetic or optical signals that carry digital data streams representing various types of information.

Network link 3220 typically provides data communication through one or more networks to other data devices. For example, network link 3220 may provide a connection through local network 3222 to a host computer 3224 or to data equipment operated by an Internet Service Provider (ISP) 3226. ISP 3226 in turn provides data communication services through the worldwide packet data communication network, now commonly referred to as the "Internet" 3228. Local network 3222 and Internet 3228 both use electrical, electromagnetic or optical signals that carry digital data streams. The signals through the various networks and the signals on network link 3220 and through communication interface 3218, which carry the digital data to and from computer system 3200, are exemplary forms of carrier waves transporting the information.

Computer system 3200 can send messages and receive data, including program code, through the network(s), network link 3220, and communication interface 3218. In the Internet example, a server 3230 might transmit a requested code for an application program through Internet 3228, ISP 3226, local network 3222 and communication interface 3218. In accordance with one or more embodiments, one such downloaded application provides for a method as disclosed herein, for example. The received code may be executed by processor 3204 as it is received, and/or stored in storage device 3210, or other non-volatile storage for later execution. In this manner, computer system 3200 may obtain application code in the form of a carrier wave.

An embodiment of the disclosure may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

Any controllers described herein may each or in combination be operable when the one or more computer programs are read by one or more computer processors located within at least one component of the lithographic apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage medium for storing such computer programs, and/or hardware to receive such medium. So the controller(s) may operate according to the machine readable instructions of one or more computer programs.

Although specific reference may be made in this text to the use of a metrology apparatus in the manufacture of ICs, it should be understood that the metrology apparatus and processes described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or one or more various other tools. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the disclosure in the context of optical lithography, it will be appreciated that the disclosure may be used in other applications, for example nanoimprint lithography, and where the context allows, is not limited to optical lithography. In the case of nanoimprint lithography, the patterning device is an imprint template or mold.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

References herein to crossing or passing a threshold may include something having a value lower than a specific value or lower than or equal to a specific value, something having a value higher than a specific value or higher than or equal to a specific value, something being ranked higher or lower than something else (through e.g., sorting) based on, e.g., a parameter, etc.

References herein to correcting or corrections of an error include eliminating the error or reducing the error to within a tolerance range.

The terms "optimizing" and "optimization" as used herein refer to or mean processes of adjusting a metrology process, lithographic apparatus, a patterning process, a parameter, etc. such that results and/or processes of metrology, lithography or patterning processing have a more desirable characteristic, such as improved accuracy, for example a higher accuracy of projection of a design layout on a substrate, a larger process window, etc. Thus, the terms "optimizing" and "optimization" as used herein refer to or mean a process that identifies one or more values for one or more variables that provide an improvement, e.g. a local optimum, in at least one relevant metric, compared to an initial set of one or more values for those one or more variables. "Optimum", "optimal" and other related terms should be construed accordingly. In an embodiment, optimization steps can be applied iteratively to provide further improvements in one or more metrics.

In an optimization process of a system, a figure of merit of the system or process can be represented as a cost function. The optimization process boils down to a process of finding a set of parameters (design variables) of the system or process that optimizes (e.g., minimizes or maximizes) the cost function. The cost function can have any suitable form depending on the goal of the optimization. For example, the cost function can be weighted root mean square (RMS) of deviations of certain characteristics (evaluation points) of the system or process with respect to the intended values (e.g., ideal values) of these characteristics; the cost function can also be the maximum of these deviations (i.e., worst deviation). The term "evaluation points" herein should be interpreted broadly to include any characteristics of the system or process. The design variables of the system can be confined to finite ranges and/or be interdependent due to practicalities of implementations of the system or process. In the case of a lithographic apparatus or patterning process, the constraints are often associated with physical properties and characteristics of the hardware such as tunable ranges, and/or patterning device manufacturability design rules, and the evaluation points can include physical points on a resist image on a substrate, as well as non-physical characteristics such as dose and focus.

While specific embodiments of the disclosure have been described above, it will be appreciated that the disclosure may be practiced otherwise than as described. For example, the disclosure may take the form of a computer program containing one or more sequences of machine-readable instructions describing a method as disclosed above, or a data storage medium (e.g. semiconductor memory, magnetic or optical disk) having such a computer program stored therein.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, third party content delivery networks may host some or all of the information conveyed over networks, in which case, to the extent information (e.g., content) is said to be supplied or otherwise provided, the information may be provided by sending instructions to retrieve that information from a content delivery network.

Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims.

Further embodiments are further described in below numbered clauses:

1. A method of determining a value of a parameter of interest of a target formed by a patterning process on a substrate, comprising:
    deriving a symmetric component and an asymmetric component of a detected pupil representation, the detected pupil representation obtainable by performing a measurement process comprising illuminating the target with radiation and detecting radiation redirected by the target,
    wherein:
        the target type and measurement process are such that a first metric characterizing the symmetric component and a second metric characterizing the asymmetric component vary non-monotonically as a function of the parameter of interest over a reference range of values of the parameter of interest; and
        the method comprises using a combination of the derived symmetric component and the derived asymmetric component to identify:
            a correct value from a plurality of candidate values of the parameter of interest that all correspond, due to the non-monotonic variation of the first metric, to a value of the first metric corresponding to the derived symmetric component for the target; or
            a correct value from a plurality of candidate values of the parameter of interest that all correspond, due to the non-monotonic variation of the second metric, to a value of the second metric corresponding to the derived asymmetric component for the target.

2. The method of clause 1, wherein the non-monotonic variation is at least approximately a periodic variation.
3. The method of clause 2, wherein the reference range of values of the parameter of interest corresponds to one period of the periodic variation.
4. The method of clause 2 or clause 3, wherein the periodic variation of the first metric has the same period as the periodic variation of the second metric.
5. The method of clause 4, wherein the periodic variation of the first metric is phase shifted relative to the periodic variation of the second metric.
6. The method of clause 5, wherein the phase shift is 90 degrees.
7. The method of any of clauses 2-6, wherein the periodic variation is at least approximately sinusoidal.
8. The method of any of clauses 1-6, wherein:
    the symmetric component and the asymmetric component are derived for each detected pupil representation of a set of detected pupil representations obtained from a corresponding set of targets; and
    the identification of the correct value of the parameter of interest comprises:
        a) deriving the first metric of the symmetric component for each target in the set of targets and using the resulting derived first metrics and corresponding values of the parameter of interest to estimate at least a sign of a rate of change of the first metric with respect to the value of the parameter of interest in a sub-region of the reference range;
        b) deriving the second metric of the asymmetric component for each target in the set of targets and using the resulting derived second metrics and corresponding values of the parameter of interest to estimate at least a sign of a rate of change of the second metric with respect to the value of the parameter of interest in the sub-region of the reference range;
            using the at least a sign of the rate of change of the first metric determined in step (a) and the at least a sign of the rate of change of the second metric determined in step (b) to identify where in the reference range the sub-region is located.
9. The method of clause 8, comprising using the identified location of the sub-region to identify the correct value from the plurality of candidate values of the parameter of interest.
10. The method of clause 8 or clause 9, wherein:
    the non-monotonic variation is at least approximately a periodic variation;
    the reference range of values of the parameter of interest corresponds to one period of the periodic variation having four quadrants; and
    the location of the sub-region is identified as follows:
        when the rate of change of the first metric is positive and the rate of change of the second metric is negative, it is determined that the sub-region is located in a first of the four quadrants;
        when the rate of change of the first metric is positive and the rate of change of the second metric is positive, it is determined that the sub-region is located in a second of the four quadrants;
        when the rate of change of the first metric is negative and the rate of change of the second metric is positive, it is determined that the sub-region is located in a third of the four quadrants; and when the rate of change of the first metric is negative and the rate of change of the second metric is negative, it is determined that the sub-region is located in a fourth of the four quadrants.

11. The method of clause 10, wherein the targets in the set of targets are selected such that the value of the parameter of interest is in the same quadrant of the reference range for all of the targets in the set.

12. The method of any of clauses 1-7, further comprising:
performing a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a value of the parameter of interest in a different one of a plurality of sub-regions of the reference range; and
performing a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a value of the parameter of interest in a different one of the plurality of sub-regions of the reference range, wherein:
the use of the combination of the derived symmetric component and the derived asymmetric component to identify the correct value of the parameter of interest comprises using the minimized fitting errors obtained by either or both of the first fitting process in different respective sub-regions and the second fitting process in different respective sub-regions to identify the sub-region in which the correct value of the parameter of interest is located.

13. The method of any of clauses 1-7, comprising:
a) performing a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a value of the parameter of interest in a different one of a plurality of sub-regions of the reference range and yields a fitted value of the parameter of interest when the fitting error is minimized;
b) selecting a subset of the sub-regions, each sub-region in the subset being a sub-region in which the minimized fitting error obtained by the first fitting process is lower than the minimized fitting error obtained by the first fitting process in all sub-regions not in the subset;
c) performing a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a different one of the fitted values of the parameter of interest obtained by the performance of the first fitting process in each sub-region of the selected subset of sub-regions and yields a fitted value of the parameter of interest when the fitting error is minimized; and
d) identifying the fitted value of the parameter of interest with the lowest minimized fitting error in step (c) as the correct value of the parameter of interest.

14. The method of clause 13, wherein:
the non-monotonic variation is at least approximately a periodic variation;
the reference range of values of the parameter of interest corresponds to one period of the periodic variation having four quadrants; and
the sub-regions in which the first fitting process is performed in step (a) comprise: a first sub-region consisting of a first of the quadrants; a second sub-region consisting of a second of the quadrants and a third of the quadrants; and a third sub-region consisting of a fourth of the quadrants; and
the subset of the sub-regions selected in step (b) consists of two of the first sub-region, second sub-region, and third sub-region.

15. The method of any of clauses 1-7, comprising:
a) performing a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a value of the parameter of interest in a different one of a plurality of sub-regions of the reference range and yields a fitted value of the parameter of interest when the fitting error is minimized;
b) selecting a subset of the sub-regions, each sub-region in the subset being a sub-region in which the minimized fitting error obtained by the second fitting process is lower than the minimized fitting error obtained by the second fitting process in all sub-regions not in the subset;
c) performing a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a different one of the fitted values of the parameter of interest obtained by the performance of the second fitting process in each sub-region of the selected subset of sub-regions and yields a fitted value of the parameter of interest when the fitting error is minimized;
d) identifying the fitted value of the parameter of interest with the lowest minimized fitting error in step (c) as the correct value of the parameter of interest.

16. The method of any of clauses 1-15, wherein the symmetric component is point symmetric with respect to a reference point in the pupil plane or mirror symmetric with respect to a reference line in the pupil plane.

17. The method of any of clauses 1-16, wherein the asymmetric component is point asymmetric with respect to a reference point in the pupil plane or mirror asymmetric with respect to a reference line in the pupil plane.

18. The method of any of clauses 1-17, wherein the parameter of interest comprises one or more of the following: a measure of an asymmetry in the target, overlay, side wall angle asymmetry, critical dimension, stack height variation.

19. A computer program product comprising a computer non-transitory readable medium having instructions recorded thereon, the instructions when executed by a computer implementing the method of any of clauses 1-18.

20. A system comprising:
    a computer system; and
    a non-transitory computer readable storage medium configured to store machine-readable instructions, wherein when executed, the machine-readable instructions cause the computer system to perform the method of any of clauses 1-18.

21. A metrology apparatus for measuring a target on a substrate, the metrology apparatus configured to perform the method of any of clauses 1-18.

22. A system comprising:
    a metrology apparatus configured to provide a beam of radiation onto a substrate and to detect radiation redirected by a target on the substrate; and
    the computer program product of clause 19.

23. The system of clause 22, further comprising a lithographic apparatus comprising a support structure configured to hold a patterning device to modulate a radiation beam and a projection optical system arranged to project the modulated radiation beam onto a radiation-sensitive substrate, wherein the lithographic apparatus is configured to control a setting of the lithographic apparatus based on information obtained using the metrology apparatus and the computer program product.

Modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, certain features may be utilized independently, and embodiments or features of embodiments may be combined, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an" element or "a" element includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every.

To the extent certain U.S. patents, U.S. patent applications, or other materials (e.g., articles) have been incorporated by reference, the text of such U.S. patents, U.S. patent applications, and other materials is only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference herein.

The descriptions above are intended to be illustrative, not limiting. Thus, it will be apparent to one skilled in the art that modifications may be made to the disclosure as described without departing from the scope of the claims set out below.

The invention claimed is:

1. A method of determining a value of a parameter of interest of a target formed by a patterning process on a substrate, the method comprising:
    deriving a symmetric component and an asymmetric component of a detected pupil representation, the detected pupil representation obtainable by performing a measurement process comprising illuminating the target with radiation and detecting radiation redirected by the target, wherein the target type and measurement process are such that a first metric characterizing the symmetric component and a second metric characterizing the asymmetric component vary non-monotonically as a function of the parameter of interest over a reference range of values of the parameter of interest; and
    using a combination of the derived symmetric component and the derived asymmetric component to identify:

a correct value from a plurality of candidate values of the parameter of interest that all correspond, due to the non-monotonic variation of the first metric, to a same value of the first metric corresponding to the derived symmetric component for the target; or a correct value from a plurality of candidate values of the parameter of interest that all correspond, due to the non-monotonic variation of the second metric, to a same value of the second metric corresponding to the derived asymmetric component for the target.

2. The method of claim 1, wherein the non-monotonic variation is at least approximately a periodic variation.

3. The method of claim 2, wherein the reference range of values of the parameter of interest corresponds to one period of the periodic variation.

4. The method of claim 2, wherein the periodic variation of the first metric has the same period as the periodic variation of the second metric.

5. The method of claim 4, wherein the periodic variation of the first metric is phase shifted relative to the periodic variation of the second metric.

6. The method of claim 5, wherein the phase shift is 90 degrees.

7. The method of claim 2, wherein the periodic variation is at least approximately sinusoidal.

8. The method of claim 1, wherein:
the symmetric component and the asymmetric component are derived for each detected pupil representation of a set of detected pupil representations obtained from a corresponding set of targets; and
the identification of the correct value of the parameter of interest comprises:
using a value of the first metric of the symmetric component for each target in the set of targets and corresponding values of the parameter of interest to estimate at least a sign of a rate of change of the first metric with respect to the parameter of interest in a sub-region of the reference range;
using a value of the second metric of the asymmetric component for each target in the set of targets and corresponding values of the parameter of interest to estimate at least a sign of a rate of change of the second metric with respect to the parameter of interest in the sub-region of the reference range; and
using the estimated at least a sign of the rate of change of the first metric and the estimated at least a sign of the rate of change of the second metric to identify where in the reference range the sub-region is located.

9. The method of claim 8, comprising using the identified location of the sub-region to identify the correct value from the plurality of candidate values of the parameter of interest.

10. The method of claim 8, wherein:
the non-monotonic variation is at least approximately a periodic variation;
the reference range of values of the parameter of interest corresponds to one period of the periodic variation and has four quadrants; and
the location of the sub-region is identified as follows:
when the rate of change of the first metric is positive and the rate of change of the second metric is negative, it is determined that the sub-region is located in a first of the four quadrants;
when the rate of change of the first metric is positive and the rate of change of the second metric is positive, it is determined that the sub-region is located in a second of the four quadrants;
when the rate of change of the first metric is negative and the rate of change of the second metric is positive, it is determined that the sub-region is located in a third of the four quadrants; and
when the rate of change of the first metric is negative and the rate of change of the second metric is negative, it is determined that the sub-region is located in a fourth of the four quadrants.

11. The method of claim 10, wherein the targets in the set of targets are selected such that the value of the parameter of interest is in the same quadrant of the reference range for all of the targets in the set.

12. The method of claim 1, further comprising:
performing a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a value of the parameter of interest in a different one of a plurality of sub-regions of the reference range; and
performing a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a value of the parameter of interest in a different one of the plurality of sub-regions of the reference range,
wherein the use of the combination of the derived symmetric component and the derived asymmetric component to identify the correct value of the parameter of interest comprises using the minimized fitting errors obtained by either or both of the first fitting process in different respective sub-regions and the second fitting process in different respective sub-regions to identify the sub-region in which the correct value of the parameter of interest is located.

13. The method of claim 1, comprising:
performing a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a value of the parameter of interest in a different one of a plurality of sub-regions of the reference range and yields a fitted value of the parameter of interest when the fitting error is minimized;
selecting a subset of the sub-regions, each sub-region in the subset being a sub-region in which the minimized fitting error obtained by the first fitting process is lower than the minimized fitting error obtained by the first
fitting process in all sub-regions not in the subset;
performing a second fitting process a plurality of times,
each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a different one of the fitted values of the parameter of interest obtained by the performance of the first fitting process in each sub-region of the selected subset of sub-regions and yields a fitted value of the parameter of interest when the fitting error is minimized; and
identifying the fitted value of the parameter of interest with the lowest minimized fitting error from the performance of the second fitting process as the correct value of the parameter of interest.

14. The method of claim 13, wherein:
the non-monotonic variation is at least approximately a periodic variation;
the reference range of values of the parameter of interest corresponds to one period of the periodic variation and has four quadrants; and
the sub-regions in which the first fitting process is performed comprise: a first sub-region consisting of a first of the quadrants; a second sub-region consisting of a second of the quadrants and a third of the quadrants; and a third sub-region consisting of a fourth of the quadrants; and
the selected subset of the sub-regions consists of two selected from: the first sub-region, the second sub-region, and the third sub-region.

15. The method of claim 1, comprising:
performing a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a value of the parameter of interest in a different one of a plurality of sub-regions of the reference range and yields a fitted value of the parameter of interest when the fitting error is minimized;
selecting a subset of the sub-regions, each sub-region in the subset being a sub-region in which the minimized fitting error obtained by the second fitting process is lower than the minimized fitting error obtained by the second fitting process in all sub-regions not in the subset;
performing a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a different one of the fitted values of the parameter of interest obtained by the performance of the second fitting process in each sub-region of the selected subset of sub-regions and yields a fitted value of the parameter of interest when the fitting error is minimized; and
identifying the fitted value of the parameter of interest with the lowest minimized fitting error from the performance of the first fitting process as the correct value of the parameter of interest.

16. A non-transitory computer-readable storage medium configured to store machine-readable instructions therein, the instructions, when executed, configured to cause a computer system to at least:
derive a symmetric component and an asymmetric component of a detected pupil representation for a target formed by a patterning process on a substrate, the detected pupil representation obtainable by performing a measurement process comprising illuminating the target with radiation and detecting radiation redirected by the target, wherein the target type and measurement process are such that a first metric characterizing the symmetric component and a second metric characterizing the asymmetric component vary non-monotonically as a function of a parameter of interest over a reference range of values of the parameter of interest; and
use a combination of the derived symmetric component and the derived asymmetric component to identify:
a correct value from a plurality of candidate values of the parameter of interest that all correspond, due to the non-monotonic variation of the first metric, to a same value of the first metric corresponding to the derived symmetric component for the target; or
a correct value from a plurality of candidate values of the parameter of interest that all correspond, due to the non-monotonic variation of the second metric, to a same value of the second metric corresponding to the derived asymmetric component for the target.

17. The computer-readable storage medium of claim 16, wherein:
the symmetric component and the asymmetric component are derived for each detected pupil representation of a set of detected pupil representations obtained from a corresponding set of targets; and
the identification of the correct value of the parameter of interest comprises:
use of a value of the first metric of the symmetric component for each target in the set of targets and corresponding values of the parameter of interest to estimate at least a sign of a rate of change of the first metric with respect to the parameter of interest in a sub-region of the reference range;
use of a value of the second metric of the asymmetric component for each target in the set of targets and corresponding values of the parameter of interest to estimate at least a sign of a rate of change of the second metric with respect to the parameter of interest in the sub-region of the reference range; and
use of the estimated at least a sign of the rate of change of the first metric and the estimated at least a sign of the rate of change of the second metric to identify where in the reference range the sub-region is located.

18. The computer-readable storage medium of claim 16, wherein the instructions are further configured to cause the computer system to use the identified location of the sub-region to identify the correct value from the plurality of candidate values of the parameter of interest.

19. The computer-readable storage medium of claim 16, wherein the instructions are further configured to cause the computer system to:
perform a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a value of the parameter of interest in a different one of a plurality of sub-regions of the reference range; and
perform a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a value of the parameter of interest in a different one of the plurality of sub-regions of the reference range,
wherein the use of the combination of the derived symmetric component and the derived asymmetric component to identify the correct value of the parameter of interest comprises use of the minimized fitting errors obtained by either or both of the first fitting process in different respective sub-regions and the second fitting process in different respective sub-regions to identify the sub-region in which the correct value of the parameter of interest is located.

20. The computer-readable storage medium of claim 16, wherein the instructions are further configured to cause the computer system to:
perform a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a value of the parameter of interest in a different one of a plurality of sub-regions of the reference range and yields a fitted value of the parameter of interest when the fitting error is minimized;
select a subset of the sub-regions, each sub-region in the subset being a sub-region in which the minimized fitting error obtained by the first fitting process is lower than the minimized fitting error obtained by the first fitting process in all sub-regions not in the subset;
perform a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a different one of the fitted values of the parameter of interest obtained by the performance of the first fitting process in each sub-region of the selected subset of sub-regions and yields a fitted value of the parameter of interest when the fitting error is minimized; and
identify the fitted value of the parameter of interest with the lowest minimized fitting error from the performance of the second fitting process as the correct value of the parameter of interest.

21. The computer-readable storage medium of claim 16, wherein the instructions are further configured to cause the computer system to:
perform a second fitting process a plurality of times, each performance of the second fitting process comprising fitting the derived symmetric component of the detected pupil representation to a symmetric component of a mathematically simulated detected pupil representation by varying one or more parameters in a mathematical model of the target used in the mathematical simulation until a fitting error is minimized, the one or more parameters including the parameter of interest, wherein each performance of the second fitting process is initiated with a value of the parameter of interest in a different one of a plurality of sub-regions of the reference range and yields a fitted value of the parameter of interest when the fitting error is minimized;
select a subset of the sub-regions, each sub-region in the subset being a sub-region in which the minimized fitting error obtained by the second fitting process is lower than the minimized fitting error obtained by the second fitting process in all sub-regions not in the subset;
perform a first fitting process a plurality of times, each performance of the first fitting process comprising fitting the derived asymmetric component of the detected pupil representation to an asymmetric component of a mathematically simulated detected pupil representation by varying one or more parameters in a mathematical model of the target used in the mathematical simulation until a fitting error is minimized, the one or more parameters including the parameter of interest, wherein each performance of the first fitting process is initiated with a different one of the fitted values of the parameter of interest obtained by the performance of the second fitting process in each sub-region of the selected subset of sub-regions and yields a fitted value of the parameter of interest when the fitting error is minimized; and
identify the fitted value of the parameter of interest with the lowest minimized fitting error from the performance of the first fitting process as the correct value of the parameter of interest.

* * * * *